(12) United States Patent
Waters et al.

(10) Patent No.: US 8,710,082 B2
(45) Date of Patent: Apr. 29, 2014

(54) BENZIMIDAZOLE INHIBITION OF BIOFILM FORMATION

(75) Inventors: Christopher Waters, East Lansing, MI (US); Karthik Sambanthamoorthy, Lansing, MI (US); Matthew Neiditch, Princeton Junction, NJ (US); Martin Semmelhack, Princeton, NJ (US)

(73) Assignee: Board of Trustees of Michigan State University, East Lansing, MI (US)

( * ) Notice: Subject to any disclaimer, the term of this patent is extended or adjusted under 35 U.S.C. 154(b) by 261 days.

(21) Appl. No.: 13/366,278

(22) Filed: Feb. 4, 2012

(65) Prior Publication Data
US 2013/0345261 A1 Dec. 26, 2013

Related U.S. Application Data

(60) Provisional application No. 61/444,531, filed on Feb. 18, 2011.

(51) Int. Cl.
*A61K 31/44* (2006.01)
*A61K 31/415* (2006.01)
*C07D 401/12* (2006.01)
*C07D 235/28* (2006.01)

(52) U.S. Cl.
USPC ..... 514/338; 514/395; 546/273.7; 548/307.1; 548/302.2

(58) Field of Classification Search
USPC ............. 514/338, 395; 546/273.7; 548/307.1, 548/302.2
See application file for complete search history.

(56) References Cited

U.S. PATENT DOCUMENTS

| 2009/0131481 A1* | 5/2009 | Alekshun et al. | 514/338 |
| 2012/0171129 A1* | 7/2012 | Melander et al. | 424/48 |
| 2013/0274256 A1* | 10/2013 | Eldridge et al. | 514/232.8 |
| 2013/0331424 A1* | 12/2013 | Weibel et al. | 514/411 |

* cited by examiner

*Primary Examiner* — Raymond Henley, III
(74) *Attorney, Agent, or Firm* — Clark IP Law, PLC

(57) ABSTRACT

The various embodiments relate to a compound comprising:

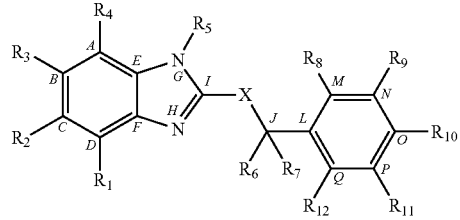

wherein $R_1$, $R_2$, $R_3$, $R_4$, $R_5$, $R_6$, $R_7$, $R_8$, $R_9$, $R_{10}$, $R_{11}$, and $R_{12}$ are each independently hydrogen, alkyl, alkenyl, alkynyl, aryl, heteroaryl, heterocyclyl, alkoxy, aryloxy, heteroaryloxy, alkoxycarbonyl, aryloxycarbonyl, heteroaryloxycarbonyl, alkylsulfonyl, arylsulfonyl, aminosulfonyl, alkylcarbonyl, arylcarbonyl, heteroarylcarbonyl, acyl, acylamino, amino, alkylamino, dialkylamino, arylamino, carboxylate (—$CO_2H$), cyano, nitro, —$CONH_2$, heteroarylamino, oxime, alkyloxime, aryloxime, amino-oxime or halogen when A, B, C, D, E, F, G, H, I, J, K, L, M, N, O, P, and Q are carbon, and X is O, NR (where R is hydrogen, alkyl, aryl or acyl), S, SO (sulfoxide), $SO_2$ (sulfone), or $C(R)_2$ (where R=H, alkyl, aryl, alkenyl, alkynyl, or acyl); or wherein $R_1$, $R_2$, $R_3$, $R_4$, $R_5$, $R_6$, $R_7$, $R_8$, $R_9$, $R_{10}$, $R_{11}$, and $R_{12}$ are each independently hydrogen or hydroxyl when A, B, C, D, E, F, G, H, I, J, K, L, M, N, O, P, and Q are each independently nitrogen, and compositions, combinations, pharmaceutically acceptable salts, esters, and prodrugs thereof. The invention also relates to methods of using such compounds and compositions.

15 Claims, 12 Drawing Sheets
(4 of 12 Drawing Sheet(s) Filed in Color)

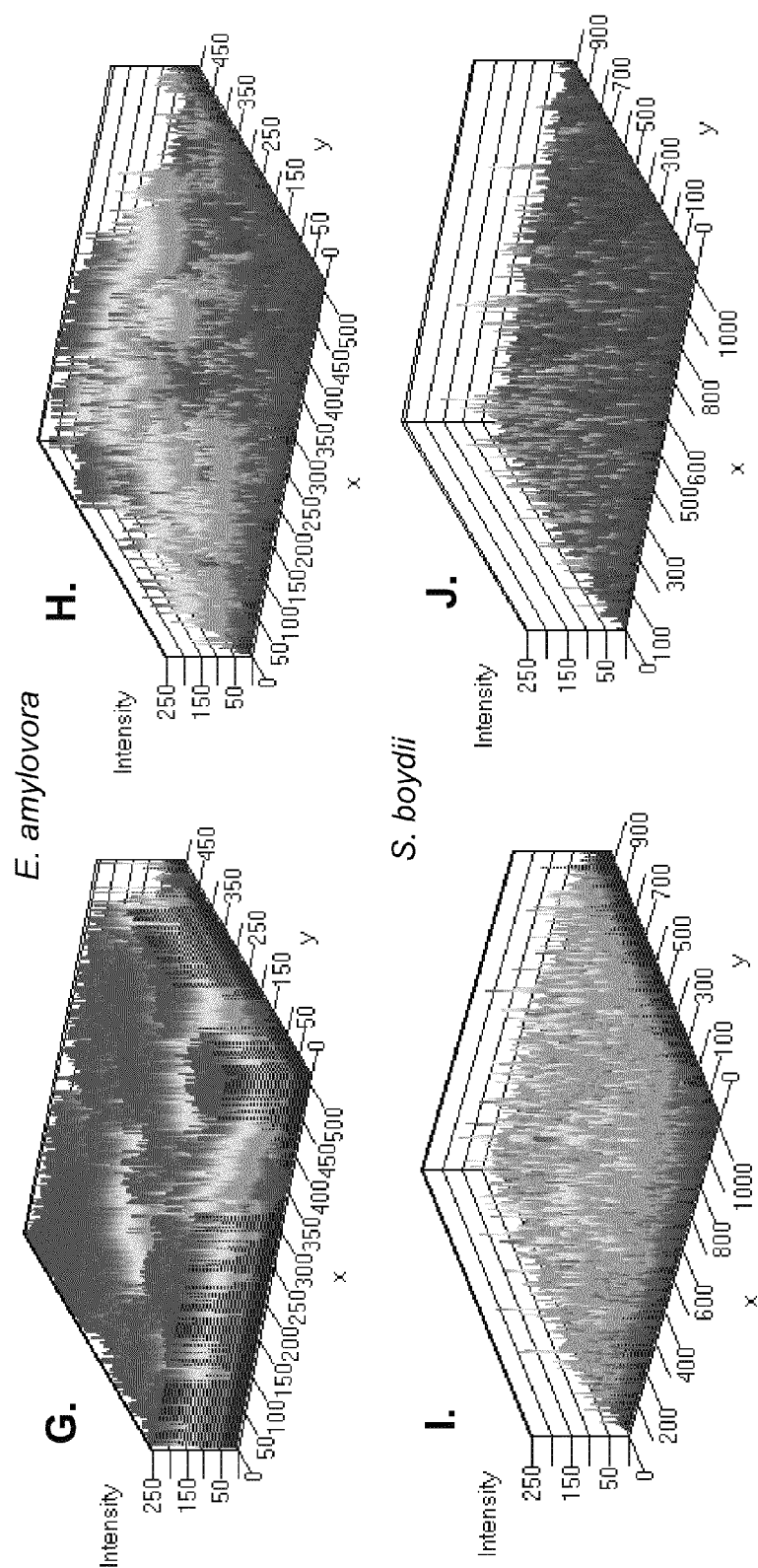
Fig. 5 (con't)

BENZIMIDAZOLE INHIBITION OF BIOFILM FORMATION

This application claims the benefit under 35 U.S.C. 119 (e) of U.S. Provisional Application Ser. No. 61/444,531 filed on Feb. 18, 2011, hereby incorporated by reference in its entirety.

STATEMENT OF GOVERNMENT RIGHTS

This invention was made with government support under R01 AI054442 and K22 AI080937 awarded by the National Institutes of Health. The government has certain rights in this invention.

BACKGROUND

Bacterial biofilm formation causes significant economic loss in industry and high morbidity and mortality in medical settings. Biofilms are defined as multicellular communities of bacteria encased in a matrix of protective extracellular polymers. Because biofilms have a high tolerance for treatment with antimicrobials, protect bacteria from immune defense, and resist clearance with standard sanitation protocols, new approaches to prevent biofilm formation are needed.

SUMMARY

In one embodiment, a novel benzimidazole molecule, namely molecule 5-methoxy-2-[(4-methylbenzyl)sulfanyl]-1H-benzimidazole, hereinafter referred to as "anti-biofilm compound 1" or "ABC-1" is provided. ABC-1 can prevent bacterial biofilm formation in multiple gram-negative and gram-positive bacterial pathogens including, but not limited to, Pseudomonas aeruginosa and Staphylococcus aureus. ABC-1 does not itself inhibit the growth of bacteria, and is effective at nanomolar concentrations. Coating of ABC-1 onto a polystyrene surface reduces biofilm formation. ABC-1 is expected to be useful as a chemical scaffold for the development of anti-biofilm compounds.

In one embodiment, the compound comprises:

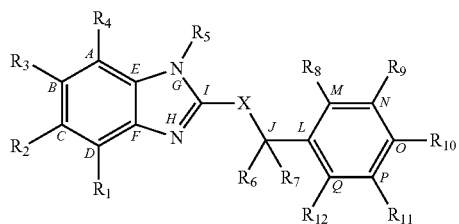

wherein $R_1$, $R_2$, $R_3$, $R_4$, $R_5$, $R_6$, $R_7$, $R_8$, $R_9$, $R_{10}$, $R_{11}$, and $R_{12}$ are each independently hydrogen, alkyl, alkenyl, alkynyl, aryl, heteroaryl, heterocyclyl, alkoxy, aryloxy, heteroaryloxy, alkoxycarbonyl, aryloxycarbonyl, heteroaryloxycarbonyl, alkylsulfonyl, arylsulfonyl, aminosulfonyl, alkylcarbonyl, arylcarbonyl, heteroarylcarbonyl, acyl, acylamino, amino, alkylamino, dialkylamino, arylamino, $CO_2H$, cyano, nitro, $CONH_2$, heteroarylamino, oxime, alkyloxime, aryloxime, amino-oxime or halogen when A, B, C, D, E, F, G, H, I, J, K, L, M, N, O, P, and Q are carbon, and X is O, NR (where R is hydrogen, alkyl, aryl or acyl), S, SO (sulfoxide), $SO_2$ (sulfone), or $C(R)_2$ (where R=H, alkyl, aryl, alkenyl, alkynyl, or acyl); or wherein $R_1$, $R_2$, $R_3$, $R_4$, $R_5$, $R_6$, $R_7$, $R_8$, $R_9$, $R_{10}$, $R_{11}$, and $R_{12}$ are each independently hydrogen or hydroxyl when A, B, C, D, E, F, G, H, I, J, K, L, M, N, O, P, and Q are each independently nitrogen, and pharmaceutically acceptable salts, esters, and prodrugs thereof.

The compounds can be used in treating a variety of conditions, including, but not limited to, endocarditis, otitis media, chronic prostatitis, periodontal disease, chronic urinary tract infection, cystic fibrosis, infections on indwelling medical devices, and chronic non-healing wounds. In some embodiments the compounds can be used to treat or inhibit infections by pathogens. Pathogen infections that can be treated or inhibited with the compounds described herein include gram negative bacterial infections, gram positive bacterial infections, as well as drug-resistant pathogens. Infections by Vibrio cholerae, P. aeruginosa, Klebsiella pneumoniae, Erwinia amylovora, Shigella boydii, and Staphylococcus aureus (e.g., MRSA types, S. aureus: Newman and S. aureus: USA300) can also be treated by administering the compounds described herein. The compounds described herein can also be used to inhibit biofilm formation by pathogens.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A, C, E, G, and I show biofilm growth in absence of ABC-1, while FIGS. 5B, D, F, H, and J show biofilm growth in presence of ABC-1. Note: Intensity mapping has set max value at 250 and maps are developed with five color layers. Additional layers of color indicate greater intensity of signal.

FIGS. 6A and C show biofilm growth in absence of ABC-1 while FIGS. 6B and D show biofilm growth in presence of ABC-1.

FIGS. 7A and C show the untreated conditions. ABC-1 was added to the cells/biofilms shown in FIGS. 7B and D after biofilms had been allowed to form for 24 hours. The images shown are 3 hours after addition of ABC-1.

DETAILED DESCRIPTION OF THE EMBODIMENTS

Figure 1:
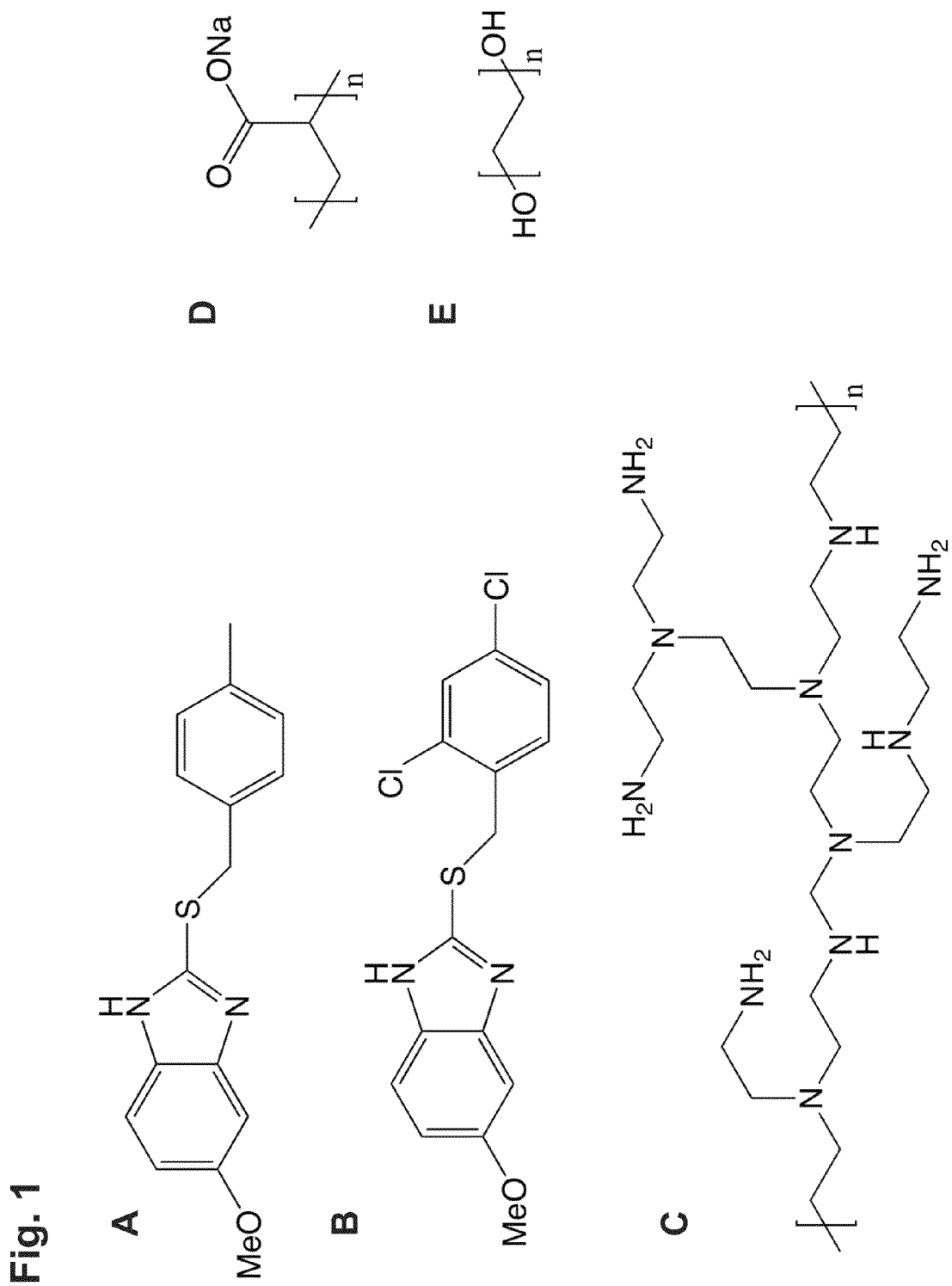
FIG. 1 shows chemical structures of ABC-1, ABC-2, and polymers used for coating. (A) structure ABC: 1-5-methoxy-2-[(4-methylbenzyl)sulfanyl]-1H-benzimidazole, (B) structure of ABC-2: 2-[(4-chlorobenzyl)thio]-5-methoxy-1H-benzimidazole, (C) Branched polyethyleneimine (BPEI), (D) Polyacrylic acid-sodium salt (PAA) and (E) Polyethylene glycol (PEG).

In the following detailed description of embodiments of the invention, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments of the present invention is defined only by the appended claims.

Biofilm formation by bacterial pathogens is an increasing cause of morbidity and mortality associated with chronic and nosocomial infections. Biofilms are defined as a conglomeration of bacterial cells protected by self-synthesized extra polymeric substance (EPS), and they are often notoriously difficult to eradicate, causing many recalcitrant infections. Bacterial biofilms are responsible for many chronic infections including dental caries, osteomyelitis and cystic fibrosis. Furthermore, biofilms are associated with 65 percent of nosocomial infections. Biofilm based infections have been estimated to be responsible for upwards of 500,000 deaths and billions of dollars in treatment costs annually in the United States alone. Therefore, new strategies to combat biofilm based infection are needed.

Unfortunately, eradication of biofilm formation during an infection is problematic. First, bacteria within a biofilm have increased tolerance to antibiotic treatment when compared to planktonic cells. This tolerance can allow biofilm based bacteria to survive 1000× the dose of antibiotics compared to their planktonic counterparts. Furthermore, biofilms are able to resist clearance by the host immune system due to exclusion of host cell antibodies and phagocytic cells. The presence of biofilms interferes with clinical therapy of chronic and wound related infections and persistent infections on various indwelling medical devices. Biofilms in wounds trigger inflammation and impair the wound healing process. Chronic non-healing wounds, which are now though to be due to biofilm formation, can often be effectively treated only through amputation of the infected limb.

Bacterial biofilm formation is also associated with significant economic losses in industrial settings. Any moist, non-sterile environment provides a fruitful ground for the development of biofilms. In industrial settings, equipment such as processing plants and cooling towers can harbor bacterial biofilms. These bacteria lead to corrosion of equipment, contamination of products, and a loss of energy efficiency. Furthermore, biofilm formation on the hulls of ships, a process known as biofouling, significantly increases drag and reduces fuel efficiency.

Traditional antibiotics and disinfectants were developed for their ability to kill or inhibit the growth of planktonic bacteria, but bacteria quickly develop resistance to such treatments. Therefore, there is a need to identify new strategies that specifically target bacteria in the biofilm state.

To this end, the inventors performed a high-throughput screen to identify molecules that would prevent bacterial biofilm formation. From this screen, the inventors determined that the molecule 5-methoxy-2-[(4-methylbenzyl)sulfanyl]-1H-benzimidazole, hereafter named Anti-Biofilm Compound 1 (ABC-1), can efficiently inhibit biofilm formation of multiple bacterial pathogens including *Vibrio cholerae, Klebsiella pneumoniae, Shigella boydii, Erwinia amylovora*, a cystic fibrosis (CF) isolate of *Pseudomonas aeruginosa*, and a Methicillin-resistant *Staphylococcus aureus* isolate (MRSA) in both static and flow conditions. In some embodiments, ABC-1 may not significantly inhibit the growth of gram-negative bacteria and may only impact the growth of gram-positive bacteria at relatively high concentrations, and therefore should lead to the lower selection for resistance. In one embodiment, ABC-1 can inhibit biofilm formation on a surface coated with ABC-1 embedded in a polymeric multi-layer matrix.

In one embodiment, various novel ABC-1 compounds are provided, including, but not limited to the following:
2-(benzylthio)-1H-benzo[d]imidazole
2-(4-methylbenzylthio)-1H-benzo[d]imidazole
2-(4-methoxybenzylthio)-1H-benzo[d]imidazole 2-(4-isopropylbenzylthio)-1H-benzo[d]imidazole
2-(3-methylbenzylthio)-1H-benzo[d]imidazole
2-(2-fluorobenzylthio)-1H-benzo[d]imidazole
2-(3-fluorobenzylthio)-1H-benzo[d]imidazole
2-(naphthalen-2-ylmethylthio)-1H-benzo[d]imidazole
2-(pyridin-4-ylmethylthio)-1H-benzo[d]imidazole
2-(benzylthio)-5-methyl-1H-benzo[d]imidazole
5-methyl-2-(4-methylbenzylthio)-1H-benzo[d]imidazole
2-(4-methoxybenzylthio)-5-methyl-1H-benzo[d]imidazole
2-(4-isopropylbenzylthio)-5-methyl-1H-benzo[d]imidazole
5-methyl-2-(3-methylbenzylthio)-1H-benzo[d]imidazole
2-(2-fluorobenzylthio)-5-methyl-1H-benzo[d]imidazole
2-(3-fluorobenzylthio)-5-methyl-1H-benzo[d]imidazole
5-methyl-2-(naphthalen-2-ylmethylthio)-1H-benzo[d]imidazole
2-(benzylthio)-5-methoxy-1H-benzo[d]imidazole
5-methoxy-2-(pyridin-4-ylmethylthio)-1H-benzo[d]imidazole
5-methoxy-2-(3-methoxybenzylthio)-1H-benzo[d]imidazole
5-methoxy-2-(4-methoxybenzylthio)-1H-benzo[d]imidazole
2-(4-isopropylbenzylthio)-5-methoxy-1H-benzo[d]imidazole
5-methoxy-2-(3-methylbenzylthio)-1H-benzo[d]imidazole
2-(2-fluorobenzylthio)-5-methoxy-1H-benzo[d]imidazole
2-(3-fluorobenzylthio)-5-methoxy-1H-benzo[d]imidazole
5-methoxy-2-(naphthalen-2-ylmethylthio)-1H-benzo[d]imidazole
2-(benzylthio)-5-fluoro-1H-benzo[d]imidazole
5-fluoro-2-(4-methylbenzylthio)-1H-benzo[d]imidazole
5-fluoro-2-(4-methoxybenzylthio)-1H-benzo[d]imidazole
5-fluoro-2-(4-isopropylbenzylthio)-1H-benzo[d]imidazole
5-fluoro-2-(3-methylbenzylthio)-1H-benzo[d]imidazole
5-fluoro-2-(2-fluorobenzylthio)-1H-benzo[d]imidazole
5-fluoro-2-(3-fluorobenzylthio)-1H-benzo[d]imidazole
5-fluoro-2-(naphthalen-2-ylmethylthio)-1H-benzo[d]imidazole
2-(benzylthio)-5-chloro-1H-benzo[d]imidazole
5-chloro-2-(4-methylbenzylthio)-1H-benzo[d]imidazole
5-chloro-2-(4-methoxybenzylthio)-1H-benzo[d]imidazole
5-chloro-2-(4-isopropylbenzylthio)-1H-benzo[d]imidazole
5-chloro-2-(3-methylbenzylthio)-1H-benzo[d]imidazole
5-chloro-2-(2-fluorobenzylthio)-1H-benzo[d]imidazole
5-chloro-2-(3-fluorobenzylthio)-1H-benzo[d]imidazole
5-chloro-2-(naphthalen-2-ylmethylthio)-1H-benzo[d]imidazole
2-(benzylthio)-5-nitro-1H-benzo[d]imidazole
2-(4-methylbenzylthio)-5-nitro-1H-benzo[d]imidazole
2-(4-methoxybenzylthio)-5-nitro-1H-benzo[d]imidazole
2-(4-isopropylbenzylthio)-5-nitro-1H-benzo[d]imidazole
2-(3-methylbenzylthio)-5-nitro-1H-benzo[d]imidazole
2-(2-fluorobenzylthio)-5-nitro-1H-benzo[d]imidazole
2-(3-fluorobenzylthio)-5-nitro-1H-benzo[d]imidazole
2-(napthalen-2-ylmethylthio)-5-nitro-1H-benzo[d]imidazole
2-(benzylthio)-1H-naphtho-[2,3-d]imidazole
2-(4-methylbenzylthio)-1H-naphtho[2,3-d]imidazole
2-(4-methoxybenzylthio)-1H-naphtho[2,3-d]imidazole
2-(4-isopropylbenzylthio)-1H-naphtho[2,3-d]imidazole
2-(3-methylbenzylthio)-1H-naphtho[2,3-d]imidazole
2-(2-fluorobenzylthio)-1H-naphtho[2,3-d]imidazole
2-(3-fluorobenzylthio)-1H-naphtho[2,3-d]imidazole
2-(naphthalen-2-ylmethylthio)-1H-naphtho[2,3-d]imidazole
2-(benzylthio)-5,6-dimethyl-1H-benzo[d]imidazole
5,6-dimethyl-2-(4-methylbenzylthio)-1H-benzo[d]imidazole
2-(4-methoxybenzylthio)-5,6-dimethyl-1H-benzo[d]imidazole
2-(4-isopropylbenzylthio)-5,6-dimethyl-1H-benzo[d]imidazole
5,6-dimethyl-2-(3-methylbenzylthio)-1H-benzo[d]imidazole
2-(2-fluorobenzylthio)-5,6-dimethyl-1H-benzo[d]imidazole
2-(3-fluorobenzylthio)-5,6-dimethyl-1H-benzo[d]imidazole
5,6-dimethyl-2-(naphthalen-2-ylmethylthio)-1H-benzo[d]imidazole The above compounds have structures identified as follows:

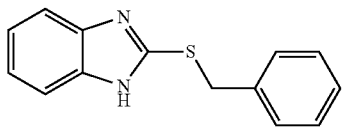

djq-7-X1Y1

2-(benzylthio)-1H-benzo[d]imidazole

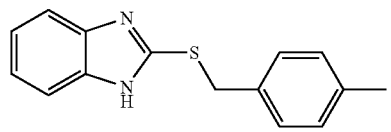

djq-7-X1Y2

2-(4-methylbenzylthio)-1H-benzo[d]imidazole

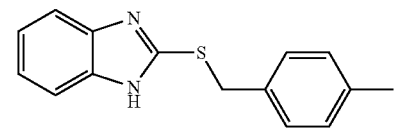

djq-7-X1Y3

2-(4-methoxybenzylthio)-1H-benzo[d]imidazole

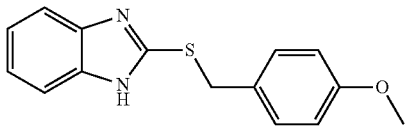

djq-7-X1Y4

2-(4-isopropylbenzylthio)-1H-benzo[d]imidazole

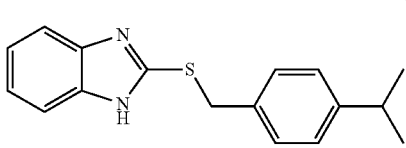

djq-7-X1Y5

2-(3-methylbenzylthio)-1H-benzo[d]imidazole

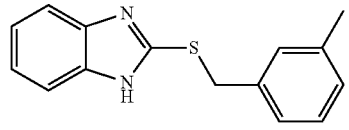

djq-7-X1Y6

2-(2-fluorobenzylthio)-1H-benzo[d]imidazole

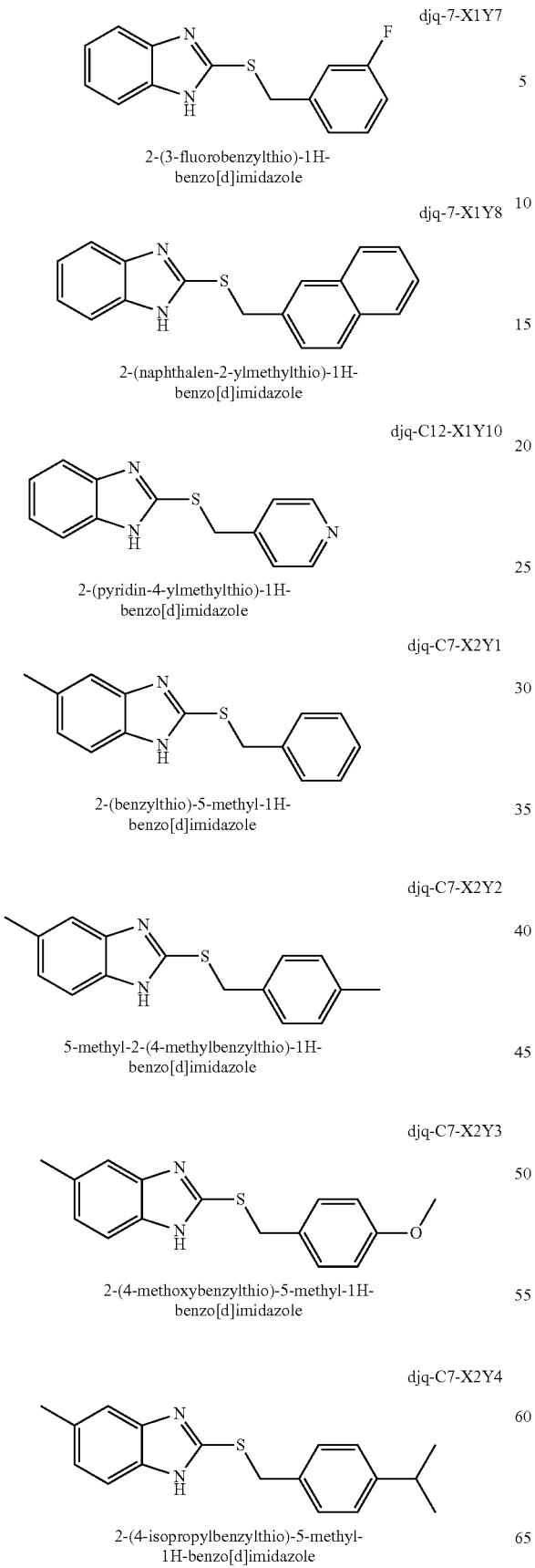
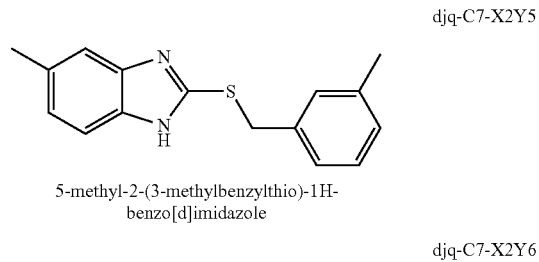

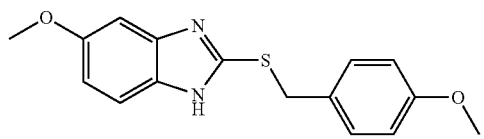

djq-C2-X3Y3

5-methoxy-2-(4-methoxybenzylthio)-
1H-benzo[d]imidazole

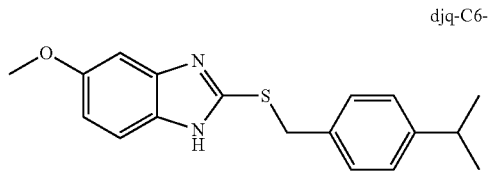

djq-C6-X3Y4

2-(4-isopropylbenzylthio)-5-methoxy-
1H-benzo[d]imidazole

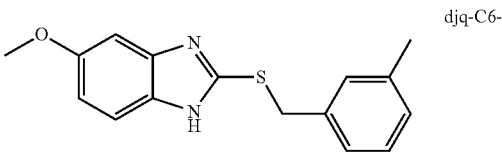

djq-C6-X3Y5

5-methoxy-2-(3-methylbenzylthio)-1H-
benzo[d]imidazole

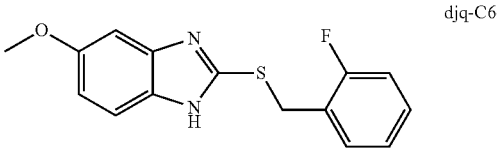

djq-C6-X3Y6

2-(2-fluorobenzylthio)-5-methoxy-1H-
benzo[d]imidazole

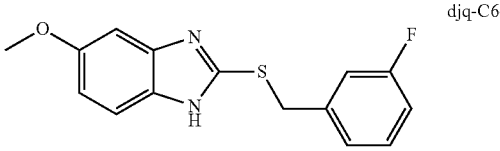

djq-C6-X3Y7

2-(3-fluorobenzylthio)-5-methoxy-
1H-benzo[d]imidazole

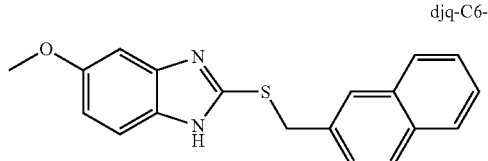

djq-C6-X3Y8

5-methoxy-2-(naphthalen-2-ylmethylthio)-
1H-benzo[d]imidazole

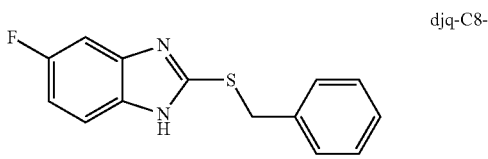

djq-C8-X4Y1

2-(benzylthio)-5-fluoro-1H-benzo[d]imidazole

djq-C8-X4Y2

5-fluoro-2-(4-methylbenzylthio)-1H-benzo[d]imidazole

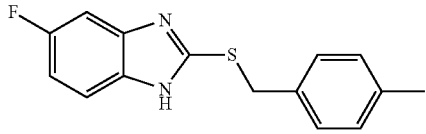

djq-C8-X4Y3

5-fluoro-2-(4-methoxybenzylthio)-1H-
benzo[d]imidazole

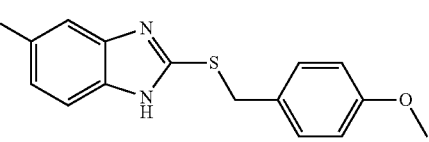

djq-C8-X4Y4

5-fluoro-2-(4-isopropylbenzylthio)-
1H-benzo[d]imidazole

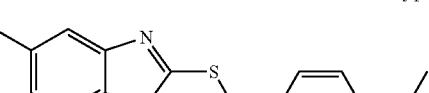

djq-C8-X4Y5

5-fluoro-2-(3-methylbenzylthio)-
1H-benzo[d]imidazole

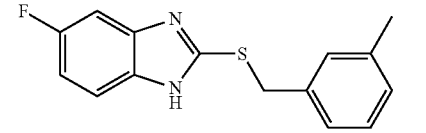

djq-C8-X4Y6

5-fluoro-2-(2-fluorobenzylthio)-1H-
benzo[d]imidazole

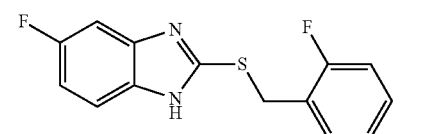

djq-C8-X4Y7

5-fluoro-2-(3-fluorobenzylthio)-1H-
benzo[d]imidazole

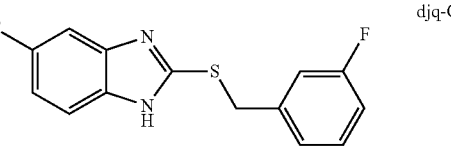

djq-C8-X4Y8

5-fluoro-2-(naphthalen-2-ylmethylthio)-
1H-benzo[d]imidazole

-continued

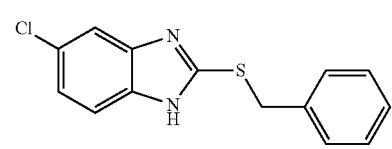

djq-C5-X5Y1

2-(benzylthio)-5-chloro-
1H-benzo[d]imidazole

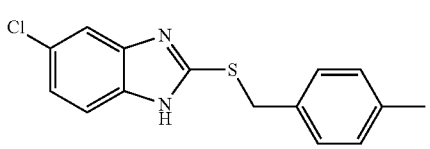

djq-C5-X5Y2

5-chloro-2-(4-methylbenzylthio)-
1H-benzo[d]imidazole

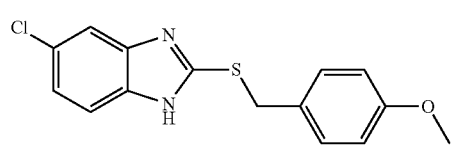

djq-C5-X5Y3

5-chloro-2-(4-methoxybenzylthio)-
1H-benzo[d]imidazole

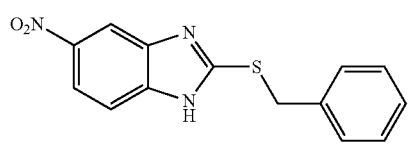

djq-C5-X5Y4

5-chloro-2-(4-isopropylbenzylthio)-
1H-benzo[d]imidazole

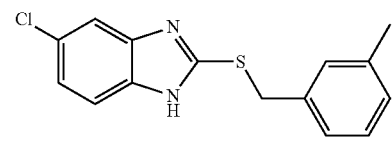

djq-C5-X5Y5

5-chloro-2-(3-methylbenzylthio)-
1H-benzo[d]imidazole

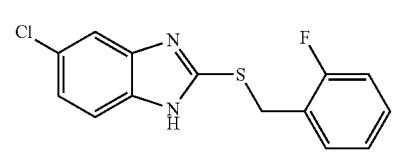

djq-C5-X5Y8

5-chloro-2-(2-fluorobenzylthio)-1H-
benzo[d]imidazole

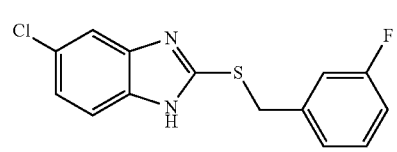

djq-C5-X5Y7

5-chloro-2-(3-fluorobenzylthio)-
1H-benzo[d]imidazole

-continued

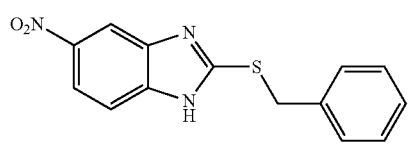

djq-C5-X5Y8

5-chloro-2-(naphthalen-2-ylmethylthio)-
1H-benzo[d]imidazole

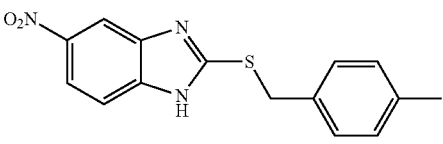

djq-9-X6Y1

2-(benzylthio)-5-nitro-1H-benzo[d]imidazole djq-9-X6Y2

2-(methylbenzylthio)-5-nitro-1H-benzo[d]imidazole

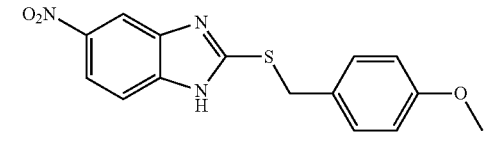

djq-9-X6Y3

2-(4-methoxybenzylthio)-5-nitro-1H-
benzo[d]imidazole

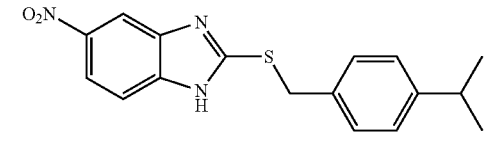

djq-9-X6Y4

2-(4-isopropylbenzylthio)-5-nitro-
1H-benzo[d]imidazole

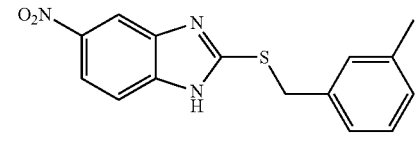

djq-X6Y5

2-(3-methylbenzylthio)-5-nitro-
1H-benzo[d]imidazole

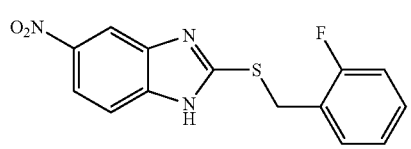

djq-9-X6Y6

2-(2-fluorobenzylthio)-5-nitro-1H-
benzo[d]imidazole djq-9-X6Y7

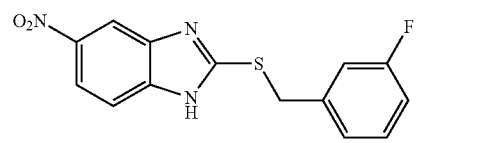

2-(3-fluorobenzylthio)-5-nitro-1H-benzo[d]imidazole djq-9-X6Y8

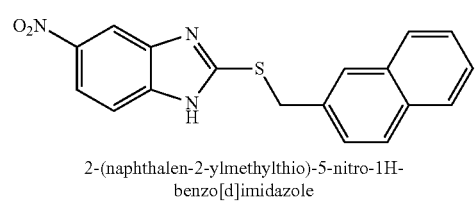

2-(naphthalen-2-ylmethylthio)-5-nitro-1H-benzo[d]imidazole djq-6-X7Y1

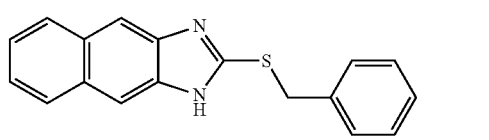

2-(benzylthio)-1H-naphtho-[2,3-d]imidazole djq-6-X7Y2

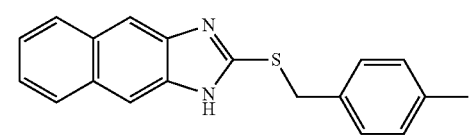

2-(4-methylbenzylthio)-1H-naphtho[2,3-d]imidazole djq-6-X7Y3

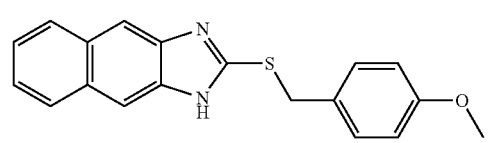

2-(4-methoxybenzylthio)-1H-naphtho[2,3-d]imidazole djq-6-X7Y4

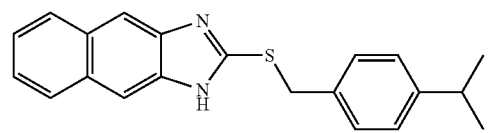

2-(4-isopropylbenzylthio)-1H-naphtho[2,3-d]imidazole djq-6-X7Y5

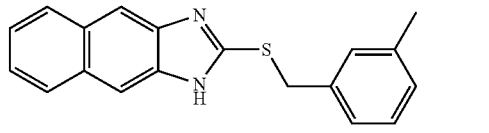

2-(3-methylbenzylthio)-1H-naphtho[2,3-d]imidazole djq-6-X7Y6

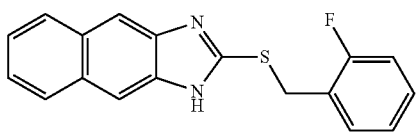

2-(fluorobenzylthio)-1H-naphtho[2,3-d]imidazole djq-6-X7Y7

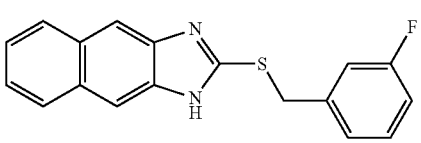

2-(3-fluorobenzylthio)-1H-naphtho[2,3-d]imidazole djq-6-X7Y8

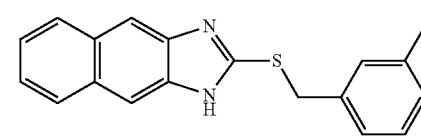

2-(naphthalen-2-ylmethylthio)-1H-naphtho[2,3-d]imidazole djq-11-X10Y1

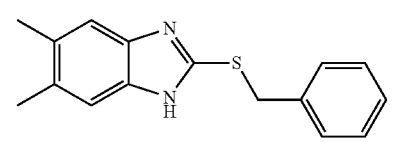

2-(benzylthio)-5,6-dimethyl)-1H-benzo[d]imidazole djq-11-X10Y2

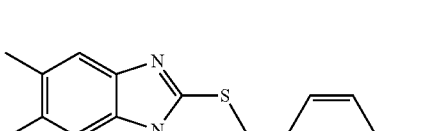

5,6-dimethyl-2-(4-methylbenzylthio)-1H-benzo[d]imidazole djq-11-X10Y3

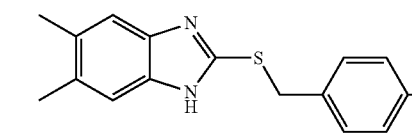

2-(4-methoxybenzylthio)5,6-dimethyl-1H-benzo[d]imidazole djq-11-X10Y4

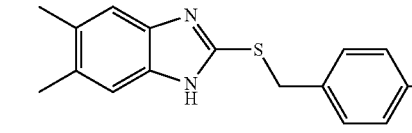

2-(4-isopropylbenzylthio)5,6-dimethyl-1H-benzo[d]imidazole

-continued

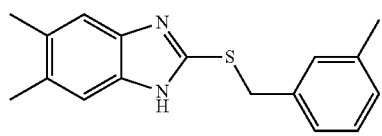

5,6-dimethyl-2-(3-methylbenzylthio)-
1H-benzo[d]imidazole

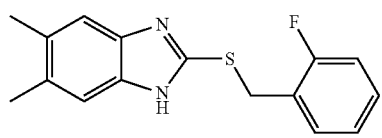

2-(2-fluorobenzylthio)-5,6-dimethyl-1H-
benzo[d]imidazole

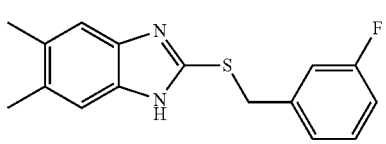

2-(3-fluorobenzylthio)-5,6-dimethyl-
1H-benzo[d]imidazole

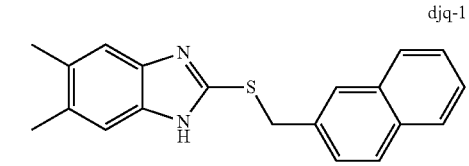

5,6-dimethyl-2-(naphthalen-2-ylmethylthio)-
1H-benzo[d]imidazole

In one embodiment, the procedure is as follows:

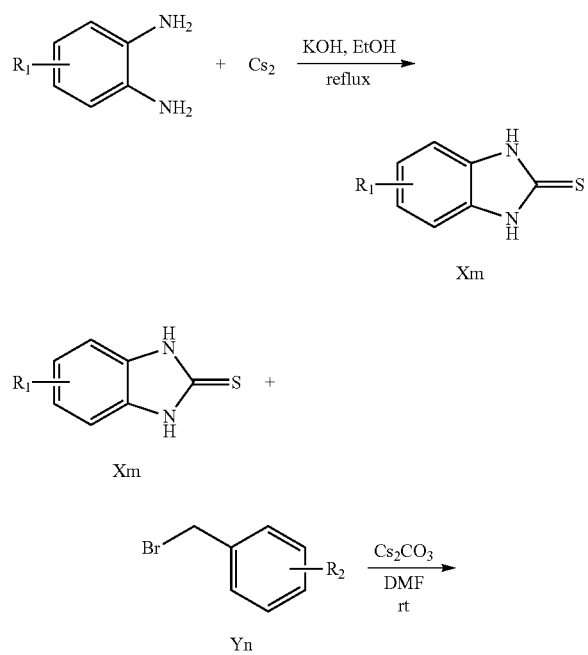

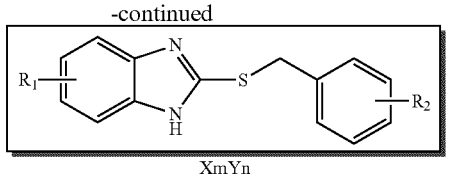

wherein for this schematic diagram of the synthetic process:

$R_1$=linear or branched alkyl, halo, nitro, alkoxy, or $R_1$ forms a cyclic, heterocyclic or aromatic ring that includes an adjacent carbon atom in the benzene ring of the Xm or XmYn indoline-2-thiol; and $R_2$=hydrogen, linear or branched alkyl, halo, alkoxy, or $R_2$ forms a cyclic, heterocyclic or aromatic ring that includes an adjacent carbon atom in the benzene ring; in some embodiments the aromatic ring joined to the $R_2$ group is a heteroaromatic ring (with 1-3 nitrogen, oxygen or sulfur heteroatoms).

Embodiments of the invention will be further described by reference to the following examples, which are offered to further illustrate various embodiments of the present invention. It should be understood, however, that many variations and modifications may be made while remaining within the scope of the present invention.

EXAMPLE 1

Materials and Methods

Bacteria and Media

The bacterial strains and plasmids used in this study are listed in Table 1 below.

TABLE 1

Strains used in this study

| Strains | Relevant genotype | Comment and/or parent strain | Source |
|---|---|---|---|
| Vibrio cholerae | ΔhapR | C6706str2 | (57) |
| Pseudomonas aeruginosa | WT | Cystic fibrosis isolate-CF 145 | Martha Mulks |
| Klebsiella pneumonia | WT | Clinical isolate | (36) |
| Erwinia amylovora | WT | Ea1189 | (11) |
| Shigella boydii | WT | 3408-67 | STEC Center at MSU |
| Staphylococcus aureus: Newman | WT | Blood isolate | ATCC 25904 |
| Staphylococcus aureus: USA300 | WT | CA-MRSA | (47) |

Vibrio cholerae, Pseudomonas aeruginosa, Klebsiella pneumoniae and Shigella boydii cells were grown at 37° C. with constant aeration in Luria Bertani broth (LB). Staphylococcus aureus cells were grown at 37° C. with constant aeration in tryptic soy broth (TSB). Erwinia amylovora was grown at 28° C. in LB broth. For biofilm growth, LB medium was used for all strains except S. aureus for which TSB medium supplemented with 0.5% glucose and 3% NaCl was used. For expression studies, Isopropyl β-D-1-thiogalactopyranoside (IPTG) was used at concentrations of 100 µM. When necessary, antibiotics were used at concentrations of kanamycin-50 µM and chloramphenicol 5 µM.

High-Throughput Screen

A total of 0.2 µL of compound (final concentration of 7.5-10 µM) was added to 20 µL of LB containing kanamycin, chloramphenicol, and IPTG in a 384-well plate. 20 µL of LB of a 1:150 dilution of an overnight culture of *V. cholerae* strain C6706str2 containing an IPTG inducible vector whereby the GGDEF VC1216 coding region was placed under the control of the Ptac promoter and a transcriptional fusion of a c-di-GMP promoter located near the gene VC1673 was added to each well. This culture was incubated overnight at 30° C. and the absorbance at $OD_{600}$ and luminescence was determined using the Pherastar plate reader. Each plate contained one row of a negative control (no compound addition) and a positive control (no IPTG addition). Preliminary experiments revealed that DMSO addition at this percentage did not affect induction of the transcriptional reporter. Approximately 66,000 compounds were screened once, and 1039 small molecules and 357 natural product extracts exhibiting greater than three standard deviations difference from the negative control were rescreened in triplicate. The top 331 compounds from this rescreen were selected and the concentration at 50% inhibition (termed $IC_{50}$) was determined in duplicate.

Synthesis of ABC-1

Preparation of 5-methoxy-2-[(4-methylbenzyl)sulfanyl]-1H-benzimidazole, ABC-1. To a mixture of 5-methoxy-2-mercaptobenzimidazole (1.673 g, 9.285 mmol) and p-xylyl bromide (1.718 g, 9.285 mmol) in DMF (33.5 mL) at 0° C., $Cs_2CO_3$ (4.53 g, 13.93 mmol) was added and the suspension was stirred for 24 h while being allow to warm from 0° C. to rt. Distilled water (150 mL) was added with vigorous stirring. The murky white suspension turned into a clearer solution with white granules. After being stirred for 20 min at rt, the mixture was filtered and the residue was rinsed with water (3×20 mL) and hexanes (3×20 mL). The crude product was >95% pure by $^1$H NMR analysis and was not further purified. The yield was 2.437 g, 92%. $^1$H NMR (500 MHz, $CDCl_3$): δ 2.25 (s, 3H), 3.76/3.78 (app d*, 3H), 4.38/4.42 (app d*, 2H), 6.74-7.17 (m, 6H), 7.52 (d, 1H, J=7.5 Hz), 8.87 (brs, 1H); $^{13}$C NMR (125 MHz, $CDCl_3$): δ 21.30, 37.39, 37.63, 55.89, 55.96, 94.15, 101.18, 110.39, 111.10, 112.45, 119.07, 128.98, 129.58, 133.94, 156.61. *The apparent doublets may arise from the 1,3-proton shift between the nitrogen atoms in the heterocycle.

Biofilm Assays

Biofilm formation was measured under both static and flow conditions. For the static condition, we used quantitative crystal violet assay on polystyrene 96-well and MBEC plates (Biosurface Technologies, Bozeman Mont.) as described previously. The MBEC technology is a 96-well plate cover containing 96 polystyrene pegs that sit in the 96 wells of a conventional plate. Briefly, overnight grown cultures were standardized to 0.1 $OD_{595}$, 200 µL was transferred to the wells of a 96-well polystyrene microtiter plate (Corning, Inc., Corning, N.Y.), and the MBEC lid was placed on top of the wells. Biofilms were grown on the pegs of the lid under shaking conditions for 24 h. The lid was removed and the pegs were gently washed twice with 200 µL of phosphate-buffered saline to remove non adherent cells. Adherent biofilms on the pegs were fixed with 200 µL of 100% ethanol prior to staining for 2 min with 200 µL of 0.41% (wt/vol) crystal violet in 12% ethanol (Protocol Crystal Violet; Biochemical Sciences, Swedesboro, N.J.). The pegs were washed several times with phosphate-buffered saline to remove excess stain. Quantitative assessment of biofilm formation was obtained by immersing the pegs in sterile polystyrene microtiter plate containing 200 µl of 100% ethanol and incubating at room temperature for 10 min (60) and the absorbance at 595 nm was determined using a SpectraMax M5 microplate spectrophotometer system (Molecular Devices, Sunnyvale, Calif.). Three independent experiments were performed for each of these assays.

For biofilm experiments under flow conditions, biofilms were grown in disposable flow cells (Stovall Life Science, Greensboro, N.C.) as described elsewhere. In brief, the inlet side of the flow cell was connected to a sterile reservoir filled with the appropriate growth medium. The outlet side was connected to a waste reservoir to create a "once-through" flow cell system. Tubing upstream of each individual cell was injected with 0.5 mL of standardized overnight culture of the test strain and the chamber was incubated in upright position at 37° C. for 1 h. Flow was then resumed with flow rate of 0.2 mL/min for *V. cholerae, P. aeruginosa, S. boydii, S. aureus* and *K. pneumoniae*, and a flow rate of 0.15 mL/min for *E. amylovora*. The non-adherent bacteria were eventually flushed by the flow of the medium thereby replacing the volume of the flow cell once every minute. Biofilm formation on the flow cell was imaged both macroscopically and microscopically at 24 h and 48 h. For biofilm dispersal studies, biofilms were allowed to develop in the flow cells for 24 h. This was followed by the addition of 100 µM ABC-1 or other compound (stock ABC-1 or other compound was dissolved in DMSO) into the growth media and biofilm dispersal was monitored at regular intervals by confocal laser scanning microscopy (CLSM).

Microscopy

For CLSM analysis of biofilms, the medium flow was stopped and fluorescent dyes syto-9 and propidium iodide (Molecular Probes, Eugene, Oreg., USA) were injected into the flow cell chamber and incubated for 30 min in the dark. Confocal microscopic images were acquired using either Olympus FluoView 1000 Laser Scanning Confocal Microscope (Olympus America Inc., Melville, N.Y.) or Carl Zeiss PASCAL Laser Scanning Microscope (Carl Zeiss, Jena, Germany) equipped with a 63×/1.4 numerical aperture Plan-Apochromat objective. The Syto-9 and propidium iodide fluorophores were exited with an argon laser at 488 nm, and the emission band-pass filters used for Syto-9 and propidium iodide were 515±15 nm and 630±15 nm, respectively. CLSM z-stack image analysis and processing were performed using either Carl Zeiss LSM 5 PASCAL Software (Version 3.5, Carl Zeiss) or the Olympus Fluoview software respectively. Image stacks of biofilms were acquired from at least three distinct regions on the flow cell. Thickness of the biofilm was measured starting from the z-section at the flow-cell/biofilm interface to the z-section at the top of the biofilm surface containing <5% of total biomass. 3D images of the biofilm were rendered using the Zeiss LSM image application.

Preparation of Anti-Microbial Compound-Polyelectrolyte-Multilayer Thin Films

Unless stated otherwise, all solutions were prepared using deionized water supplied by a Barnstead Nanopure-UV 4 stage purifier (Barnstead International Dubuque, Iowa), equipped with a UV source and a final 0.2 µm filter, with resistivity greater than 18 MΩ·cm. The polymers used in this study were Branched polyethyleneamine, polyacrylic acid and polyethylene glycol (FIGS. 1C, D and E). Branched polyethylenimine (BPEI) ($M_w$ approximately 25,000 daltons), polyacrylic acid (PAA) sodium salt (35 wt-% solution in water, $M_w$ approximately 15,000 daltons) and polyethylene glycol (PEG) ($M_v$, approximately 10,000 daltons) were purchased from Sigma-Aldrich, St. Louis, Mo. The concentration of BPEI, PAA and PEG was maintained at 1 mg/mL. Deposition of the multilayers was performed by standard procedures. In brief, an automated Carl-Zeiss slide-stainer with a custom designed ultra-sonic bath was used to deposit multilayers as described by on the polystyrene surface of the MBEC assay plate. The robotic arm of the slide-stainer to which the MTBE assay plate is attached, can be programmed to carry out the immersion, washing and sonication steps for the specified period of time. Before depositing the multilayers, the surface of the polystyrene plate was extensively cleaned using a Harrick plasma cleaner (Harrick Scientific Corporation, Broading Ossining, N.Y.) for 15 min. The pressure and oxygen flow-rate in the plasma chamber was maintained at 0.15 Torr and 50 sccm respectively as described by.

The anti-biofilm compound-incorporated-multilayers were deposited using an approach similar to that described elsewhere (55). Briefly speaking, the $O_2$-plasma cleaned plate was dipped in BPEI solution as prepared above, (pH adjusted to approximately 10.5) for 30 min followed by dipping in DI water (pH=10.5) twice for 10 min each to remove the loosely bound polymer. Thereafter, the plate was dipped in PAA and PEG solutions for 20 min each (pH adjusted to 2.0) to deposit one bilayer. After every polymer dipping cycle, the plate was washed twice with DI water (pH 2.0). Five such bilayers of PAA/PEG were deposited. PEG formed the terminating layer.

Ten mg of ABC-1 dissolved in 2 mL Dimethyl sulfoxide (DMSO) was subsequently diluted to 100 μM by adding DI water (pH 2.0). Five and one-half bilayers of compound/PEG were deposited on the PAA/PEG coated plate using the same immersion and washing steps as described above. ABC-1 formed the terminating layer. The plate was cured for 30 min using a UV sterilizer once the multilayer deposition was complete.

Results

ABC-1 and ABC-2 Inhibit Biofilm Formation in *V. cholerae*

Approximately 66,000 compounds and natural product extracts were screened by the inventors at the Center for Chemical Genomics at the University of Michigan to identify novel compounds that inhibit biofilm formation. The hypothesis was to identify small molecules that negatively impacted induction of a *Vibrio cholerae* cyclic di-GMP (c-di-GMP) inducible transcriptional fusion. C-di-GMP is a newly appreciated second messenger signal found in the majority of all bacteria that induces biofilm formation. Therefore, the inventors reasoned that compounds that could reduce expression of the transcriptional reporter would have anti-biofilm properties, either through a reduction in the levels of c-di-GMP or via other mechanisms.

The transcription fusion used in the screen encoded a c-di-GMP induced promoter we have recently identified located in the VC1673 gene (unpublished results) fused to a luciferase reporter. This fusion was inserted into a *V. cholerae* strain in which the levels of c-di-GMP were artificially induced through overexpression of the c-di-GMP synthesis enzyme, VC1216, encoded on a second plasmid. Compounds and natural product extracts were screened in a 384-well format. In addition to measuring luciferase expression, growth was simultaneously quantified by reading the $OD_{600}$ of each well. Compounds that inhibited luciferase expression at levels greater than three standard deviations from the negative control wells without significantly impacting growth were considered hits and screened further in triplicate. Dose response curves were performed in duplicate on the top 301 hits to determine the concentration of each compound that inhibits luciferase expression 50% ($IC_{50}$). Importantly, the screen was performed using intact, growing bacteria. Therefore, any hits that show activity must be able to cross the lipid bilayer of bacteria (or signal from the outside). Moreover, the inventors excluded from further analysis any compounds that significantly inhibited the growth of bacteria because it was hypothesized that anti-infective strategies that reduce virulence without blocking or inhibiting growth will lead to less selection for resistant strains.

Figure 2:
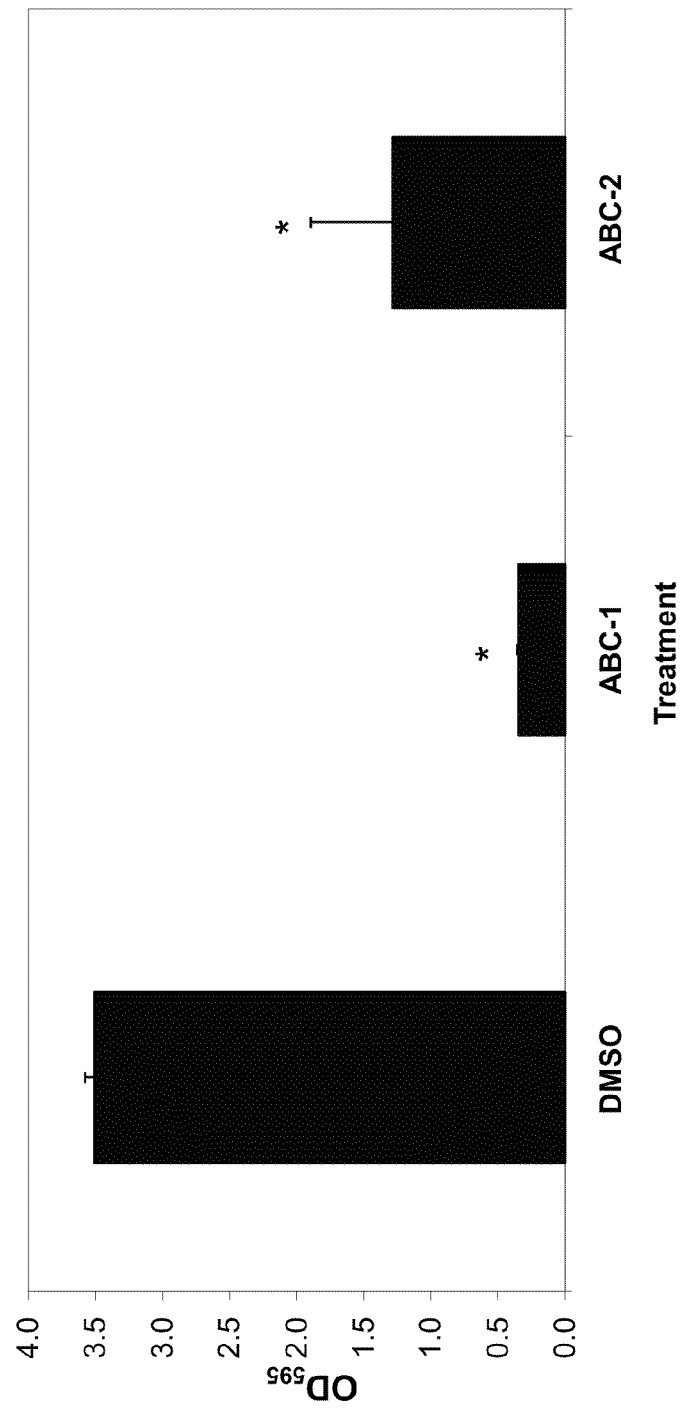
FIG. 2 shows ABC-1 and ABC-2 inhibit biofilm formation of V. cholerae. V. cholerae was grown in LB medium for 8 hours in the wells MBEC plates with 10 µM ABC-1, ABC-2, or the equivalent amount of DMSO. Biofilm was quantified by staining with crystal violet and elution with ethanol as described in text according to illustrative embodiments of the present invention. Results represent the mean±SEM. Student's paired t-test was used to determine statistical significance (*denotes statistical significance of P<0.05).

From the screen, the inventors identified 188 compounds that inhibited VC1673-lux with an $IC_{50}$ lower than 10 μM. Here, the activities of two structurally related benzimidazole compounds from this group are described in more detail, 5-methoxy-2-[(4-methylbenzyl)sulfanyl]-1H-benzimidazole, named anti-biofilm compound 1 (ABC-1) and 2-[(4-chlorobenzyl)thio]-5-methoxy-1H-benzimidazole named anti-biofilm compound 2 (ABC-2) that showed anti-biofilm activities (FIGS. 1A and B). To examine the anti-biofilm properties of ABC-1 and ABC-2, *V. cholerae* was grown in the presence of 100 μM ABC-1 and ABC-2, and biofilm formation was determined using the MBEC crystal-violet biofilm assay (see materials and methods). Each of these compounds was capable of significantly inhibiting *V. cholerae* biofilm development (FIG. 2). However, the inventors chose to more fully characterize the anti-biofilm activity of ABC-1.

ABC-1 is a Broad-Spectrum Inhibitor of Biofilm Formation

Figure 3:
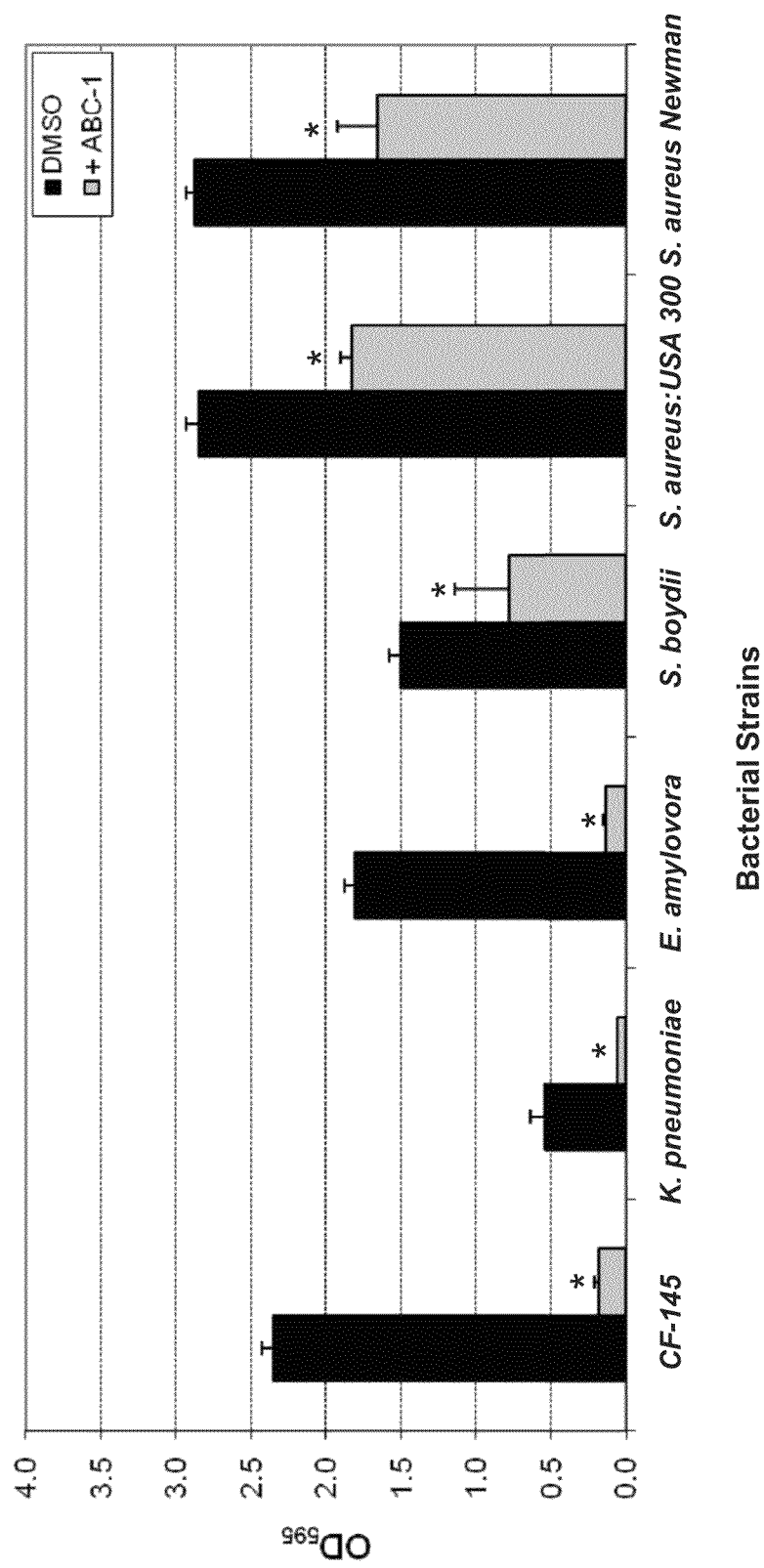
FIG. 3 shows ABC-1 exhibits broad-spectrum anti-biofilm activity. Cultures were incubated in the wells of MBEC plates, and biofilm formation was quantified by staining with crystal violet and elution with ethanol as described in text. Results represent the mean±SEM according to illustrative embodiments of the present invention. A paired t test was used to determine statistical significance of the treated versus untreated conditions (*denotes statistical significance of P<0.05).

ABC-1 possessed potent anti-biofilm activity towards *V. cholera*. However, the most useful compounds generally possess broad-spectrum anti-biofilm properties against a number of different bacterial pathogens. The inventors therefore examined the activity of ABC-1 to inhibit biofilm formation of five human pathogens and one plant pathogen in the MBEC static biofilm assay. The bacteria selected for examination were a CF clinical isolate of *Pseudomonas aeruginosa* (CF-145), *Klebsiella pneumoniae*, *Erwinia amylovora*, *Shigella boydii*, *Staphylococcus aureus* MRSA strain USA3000, and *S. aureus* strain Newman. The rationale for examining each of these species of bacteria is given below. ABC-1 was used at concentrations between 50 and 100 μM for select pathogens. Similar to the results observed for *V. cholerae*, ABC-1 significantly inhibited biofilms in each of these bacteria in the MBEC static biofilm assay (FIG. 3). These data show that ABC-1 possesses broad-spectrum anti-biofilm activity against multiple bacterial pathogens.

Figure 4:
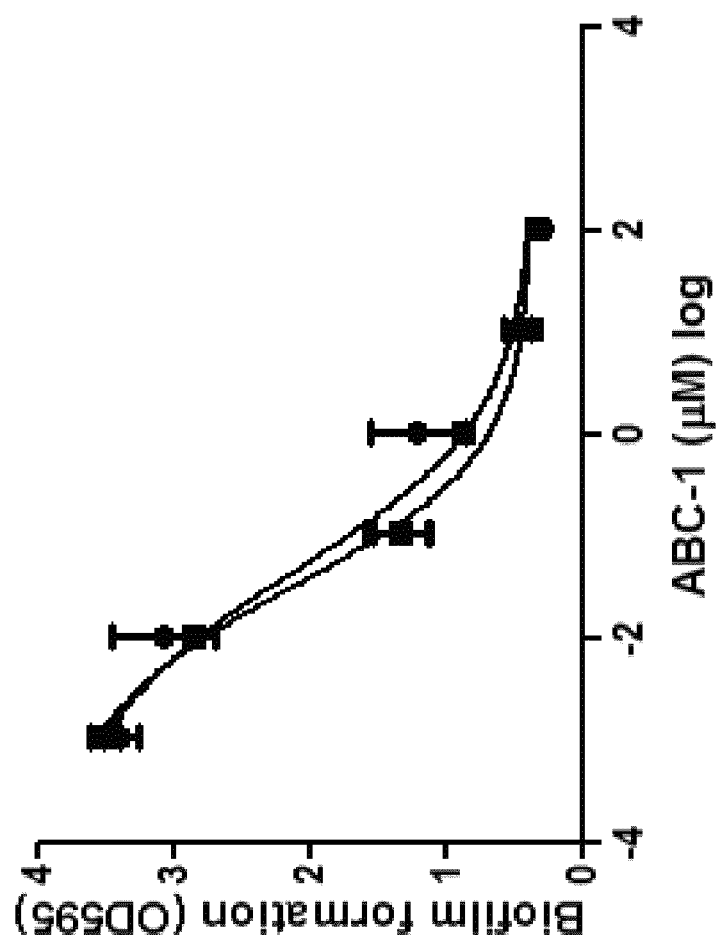
FIG. 4 shows ABC-1 inhibits biofilm formation of V. cholerae and P. aeruginosa at nanomolar concentrations. A concentration response curve measuring the anti-biofilm activity of ABC-1 was performed in duplicate. P. aeruginosa and V. cholera are represented as circles and squares, respectively. The calculated $IC_{50}$ of P. aeruginosa is 45.9 nM with a 95% confidence interval of 44.3 to 47.5. The $IC_{50}$ V. cholera is 32.3 nM with a 95% confidence interval of 14.1 to 74.4.

ABC-1 is active against *V. cholerae* and *P. aeruginosa* at nM concentrations. The $IC_{50}$ to inhibit biofilm formation for both *V. cholerae* and the *P. aeruginosa* CF-145 was determined using the MBEC assay by measuring biofilm formation of these bacteria in duplicate for a range of ABC-1 concentrations. The data were fit to a log(inhibitor) vs. response curve using a nonlinear regression with variable slope analysis by the software Prism. The $IC_{50}$ value of ABC-1 to inhibit biofilm formation of *V. cholerae* was 32.3 nM with a 95% confidence interval from 14.1 to 74.4 nM. Similarly, the calculated $IC_{50}$ value of ABC-1 to inhibit biofilm formation of *P. aeruginosa* was 45.9 nM with a 95% confidence interval of 44.3 to 47.5 nM (FIG. 4). Thus, ABC-1 possesses anti-biofilm activities at nM concentrations and inhibits biofilm formation at a similar concentration in both *V. cholerae* and *P. aeruginosa*.

ABC-1 Inhibits Biofilm Formation of *V. cholerae* Under Flow Conditions

The results obtained thus far showed that ABC-1 possessed broad-spectrum anti-biofilm activity towards inhibition of biofilm formation in static conditions. However, natural biofilms and biofilm associated with disease typically form in environments exposed to fluid flow. Therefore, the inventors analyzed the impact of ABC-1 on biofilm formation using flow-cells exposed to a continuous flow of fresh media to better approximate physiological relevant biofilm formation.

First, *V. cholerae* biofilm formation was measured using a flow-cell apparatus that enabled a noninvasive observation of biofilm formation under a continuous flow in the presence and absence of 10 µM ABC-1. After 24 hours, the biofilms were stained with a Live/Dead cell viability assay stain to differentiate between intact and compromised cells, and biofilms were visualized using confocal-laser scanning microscopy (CLSM). This analysis permitted generation of a three-dimensional view of the biofilm through the measurement of signal intensity. The biofilm structure can be observed as an intensity map in FIGS. 5A and 5B where the intensity of the signal represents the density of cells in a particular location. These results show that growth of *V. cholerae* in 10 µM ABC-1 under shear conditions dramatically reduced biofilm formation, consistent with the inventors' observations in static conditions.

ABC-1 Inhibits Biofilm Formation in Multiple Gram-Negative Pathogens

*V. cholerae* persists as biofilms in environmental reservoirs, but the importance of biofilm formation during infection remains unclear. Therefore, the inventors determined the ability of ABC-1 to inhibit biofilm formation by several pathogens in which biofilm formation is an important virulence determinant. One such pathogen is *Pseudomonas aeruginosa*, the most prominent pathogen in lung infections of cystic fibrosis (CF) individuals. Biofilm formation by *P. aeruginosa* during a CF infection is hypothesized to be an important survival strategy in colonized lung. Over time, *P. aeruginosa* colonizing the lung mutate into a mucoid biotype, which is associated with higher levels of cyclic di-GMP and robust biofilm formation. The mucoid biotype leads to chronic colonization that cannot be cleared with antibiotic treatment. Although aggressive antibiotic therapy can reduce the rate of lung damage, these chronic infections eventually lead to lung failure necessitating the need for a lung transplant.

Figure 5:
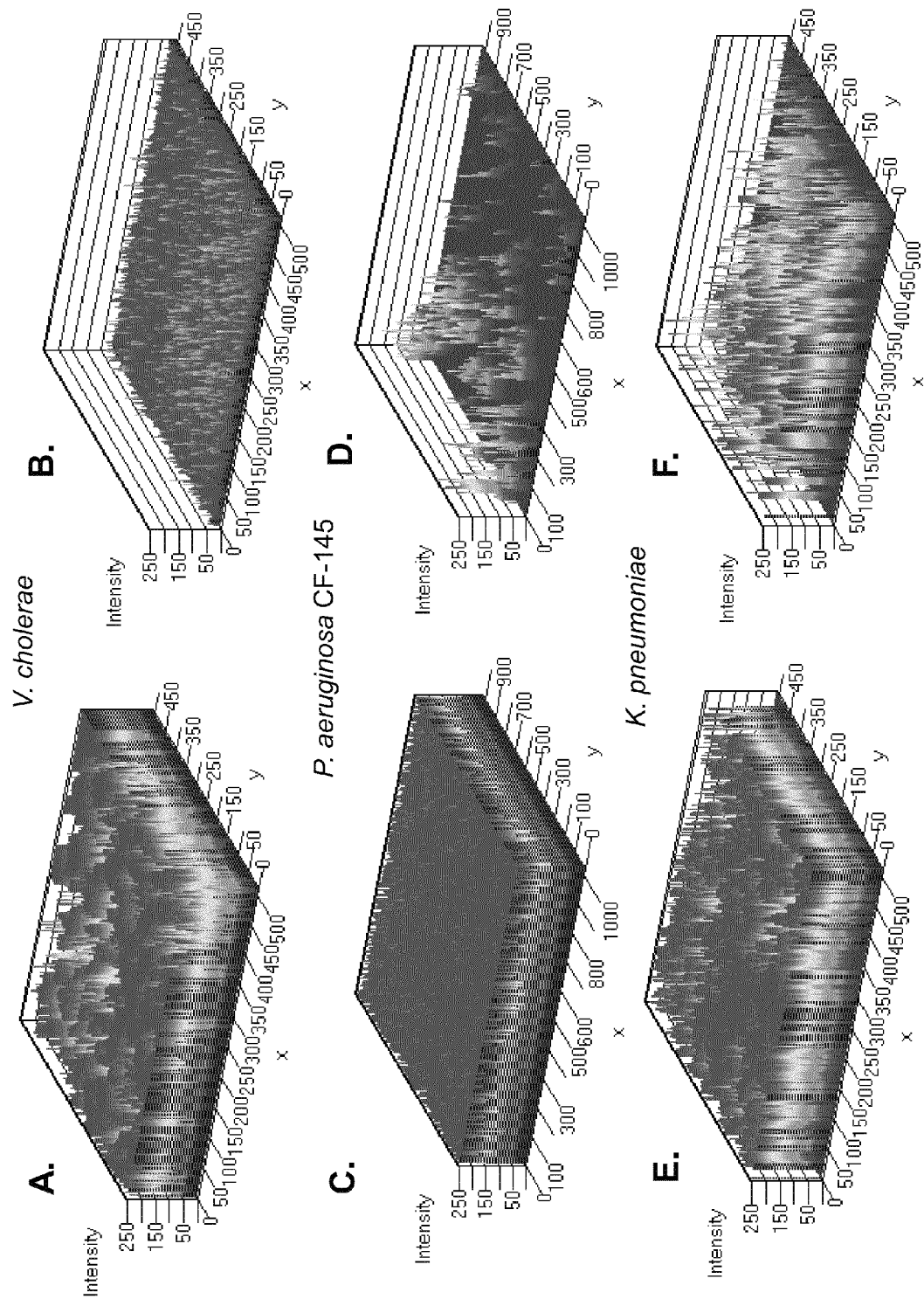
FIG. 5 shows how ABC-1 inhibits biofilm formation of multiple gram-negative pathogens under flow according to illustrative embodiments of the present invention. Three-dimensional views are shown of biofilm in flow cells through intensity mapping after 24-48 h of growth of the following: V. cholera (A, B), P. aeruginosa CF-145 (C, D), K. pneumonia (E, F), E. amylovora (G, H), and S. boydii (I, J).

The CF-145 *P. aeruginosa* strain that we had examined in the MBEC assay is a mucoid isolate (FIG. 3). Similar to our results in static conditions, ABC-1 possessed potent anti-biofilm activity against the CF strain under flow conditions. In the untreated flow chamber, biofilm growth was observed throughout the entire chamber, attached to the surface and exhibiting vertical growth (FIG. 5C). In contrast, *P. aeruginosa* treated with 100 µM ABC-1 had greatly reduced biofilm formation. ABC-1 treatment led to a low signal intensity of fluorescence and no signs of aggregation after 24 h (FIG. 5D). Also, similar results were obtained when a laboratory isolate of *P. aeruginosa* (strain PA01) was treated with ABC-1 (data not shown).

The inventors also determined the anti-biofilm activity of ABC-1 against *Klebsiella pneumoniae* in flow conditions. *K. pneumoniae* is an important opportunistic pathogen commonly associated with nosocomial urinary tract infections (UTIs), including catheter-associated UTIs (CAUTIs), as well as sepsis and pneumonia (63). ABC-1 treatment of *K. pneumoniae* inhibited biofilm formation in flow conditions at 24 hours in both static MBEC assays (FIG. 3) and continuous flow conditions (FIGS. 5E and F). In the untreated flow cell, thick cellular aggregates were present throughout the flow cell chamber (FIG. 5E), while this characteristic feature was absent in ABC-1 treatment cells accompanied with less surface coverage (FIG. 5F). In addition, the biofilms that did form in the presence of ABC-1 began to disperse beyond 30 hours while the untreated *K. pneumoniae* continued to make uniform biofilms (data not shown).

*Erwinia amylovora*, the causative agent of fire-blight infections, leads to wilting of infected plants by blocking xylem function through the formation of biofilms. Therefore, we determined the anti-biofilm activity of ABC-1 on *E. amylovora*. Identical to our above results, addition of 100 µM ABC-1 displayed a pronounced decrease in the *E. amylovora* biofilm development under both static (FIG. 3) and in continuous flow conditions (FIGS. 5G and H). Untreated *E. amylovora* developed thick biofilms whereas ABC-1 treated *E. amylovora* showed more sparse distribution of biofilms in the flow chamber (FIG. 5H).

Next the anti-biofilm activity of ABC-1 was examined against *Shigella boydii*, a pathogen known to cause to dysentery in humans through fecal-oral contamination. *S. boydii* is a prominent pathogen in the food produce sector where biofilm formation in food processing equipment has been implicated in foodborne outbreaks. Furthermore, it has been previously demonstrated that *S. boydii* has the potential to persist and form biofilms on the surface of parsley plants, which may be another mechanism of product contamination. This feature contributes to the ineffectiveness of aqueous sanitizers in inactivating human pathogens found on plant tissues. Therefore, anti-biofilm strategies targeting *S. boydii* that can be either used alone or in combination with sanitizers to prevent biofilm formation are much needed. As seen with the other bacteria examined, development of *S. boydii* biofilms were significantly impacted upon treatment with 100 µM ABC-1 in both static (FIG. 3) and flow conditions (FIGS. 5I and 5J). *S. boydii* produced less robust biofilm formation in the conditions examined compared with the other pathogens studied. Nevertheless, at 48 h, biofilm formation by *S. boydii* in the flow chamber was observed (FIG. 5I). Treatment with ABC-1 greatly reduced biofilm formation of *S. boydii* (FIG. 5J). It should be noted that ABC-1 treatment at the concentrations used had no impact on growth of any of the bacteria examined (data not shown).

ABC-1 Inhibits Biofilm Formation of *Staphylococcus aureus*

The above results show that ABC-1 possesses broad-spectrum anti-biofilm activity against multiple gram-negative bacterial pathogens. However, gram-positive bacteria like *Staphylococcus aureus*, *Staphylococcus epidermidis*, and *Streptococcus* are problematic biofilm-forming pathogens. *S. aureus* is one of the most important pathogens that cause infections associated with indwelling medical devices such as prosthetic joints, prosthetic heart valves and intravascular catheters, thereby creating an enormous health care problem.

Figure 6:
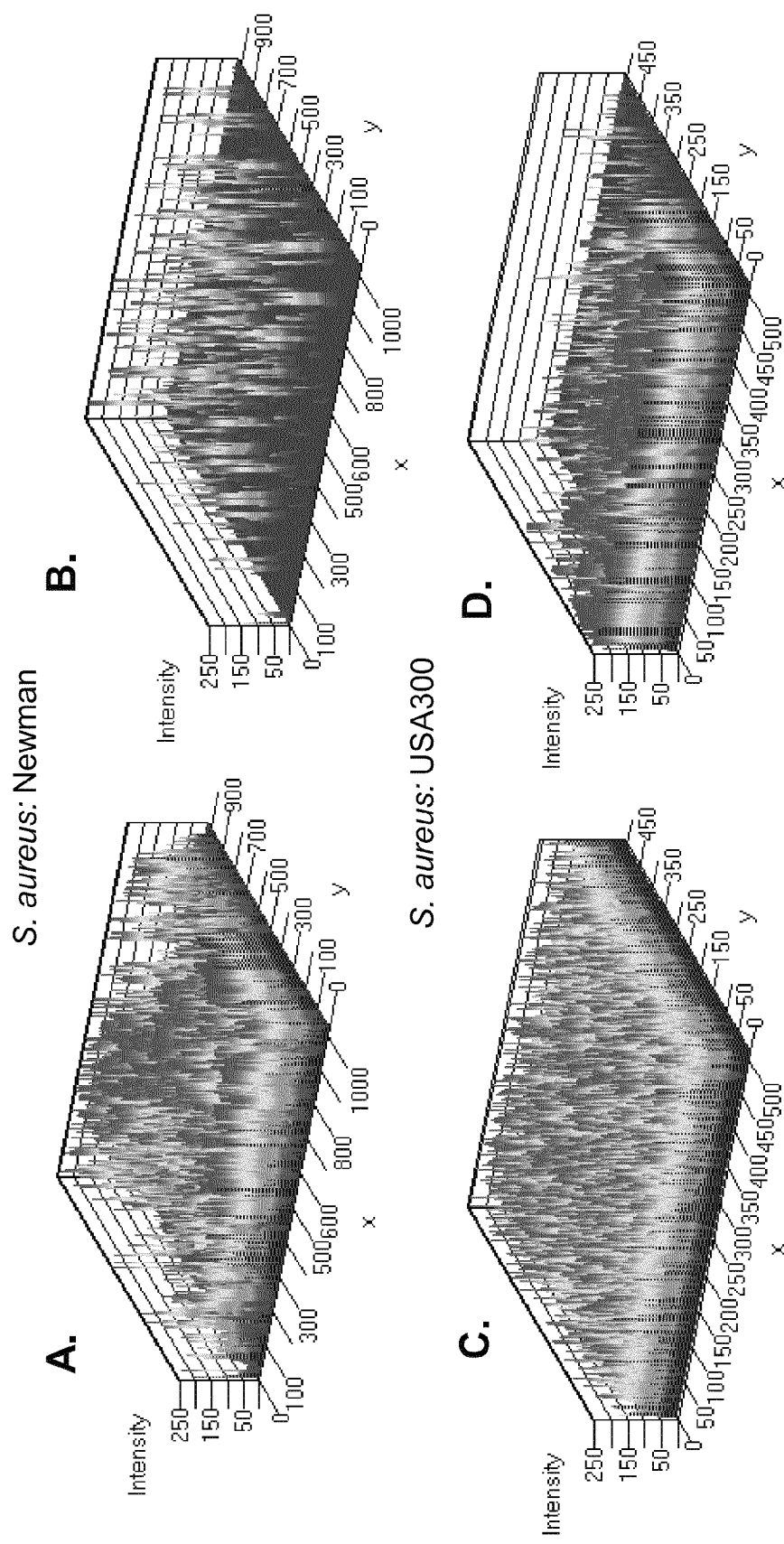
FIG. 6 shows how ABC-1 inhibits biofilm formation of *S. aureus* under flow according to illustrative embodiments of the present invention. Three-dimensional view of biofilm in flow cells is shown through intensity mapping of *S. aureus*: Newman (A and B) and *S. aureus*: USA300 (C and D).

To examine if ABC-1 exhibits anti-biofilm properties against gram-positive bacteria, the inventors examined the activity of ABC-1 on two strains of the gram positive-pathogen *S. aureus:* 1) *S. aureus* Newman, a blood isolate and 2) and a USA-300 community acquired Methicillin-Resistant *Staphylococcus aureus* (CA-MRSA). Before examining the anti-biofilm properties of ABC-1, we initially determined the impact of ABC-1 on the growth of *S. aureus*. From these studies, we found that concentrations of ABC-1 at 50 µM or greater inhibited the growth of *S. aureus* (data not shown). This finding is in contrast with the results with gram-negative bacteria in which no concentration of ABC-1 showed inhibition of growth. Because the focus was upon the anti-biofilm activity of ABC-1 rather than killing the bacteria, the inventors examined of the impact of 25 µM ABC-1 on biofilm formation of *S. aureus* to avoid activity due to toxicity effects of the compound. Inhibition of biofilm formation of both *S. aureus* strains in static conditions was observed to be statistically significant ($P<0.05$), but less robust than observed for most gram-negative pathogens (FIG. 3). However, greater inhibition of biofilms by ABC-1 was observed under flow conditions. When subjected to shear conditions, *S. aureus* strain Newman in the absence of ABC-1 formed significant biofilm on the surface of the flow cell (FIG. 6A). The biofilm was patchy and consisted of numerous mushroom-like structures. In contrast, ABC-1 treated *S. aureus* exhibited less surface area coverage and biofilms were present as small patches (FIG. 6B). Similarly, biofilm formation of CA-MRSA in the presence of ABC-1 was reduced compared to the untreated condition (FIGS. 6C and D). These continuous flow condition experiments on *S. aureus* revealed that ABC-1 treatment significantly decreased biofilm formation by *S. aureus* Newman and CA-MRSA.

Impact of ABC-1 on Biofilm Dispersion

Figure 7:
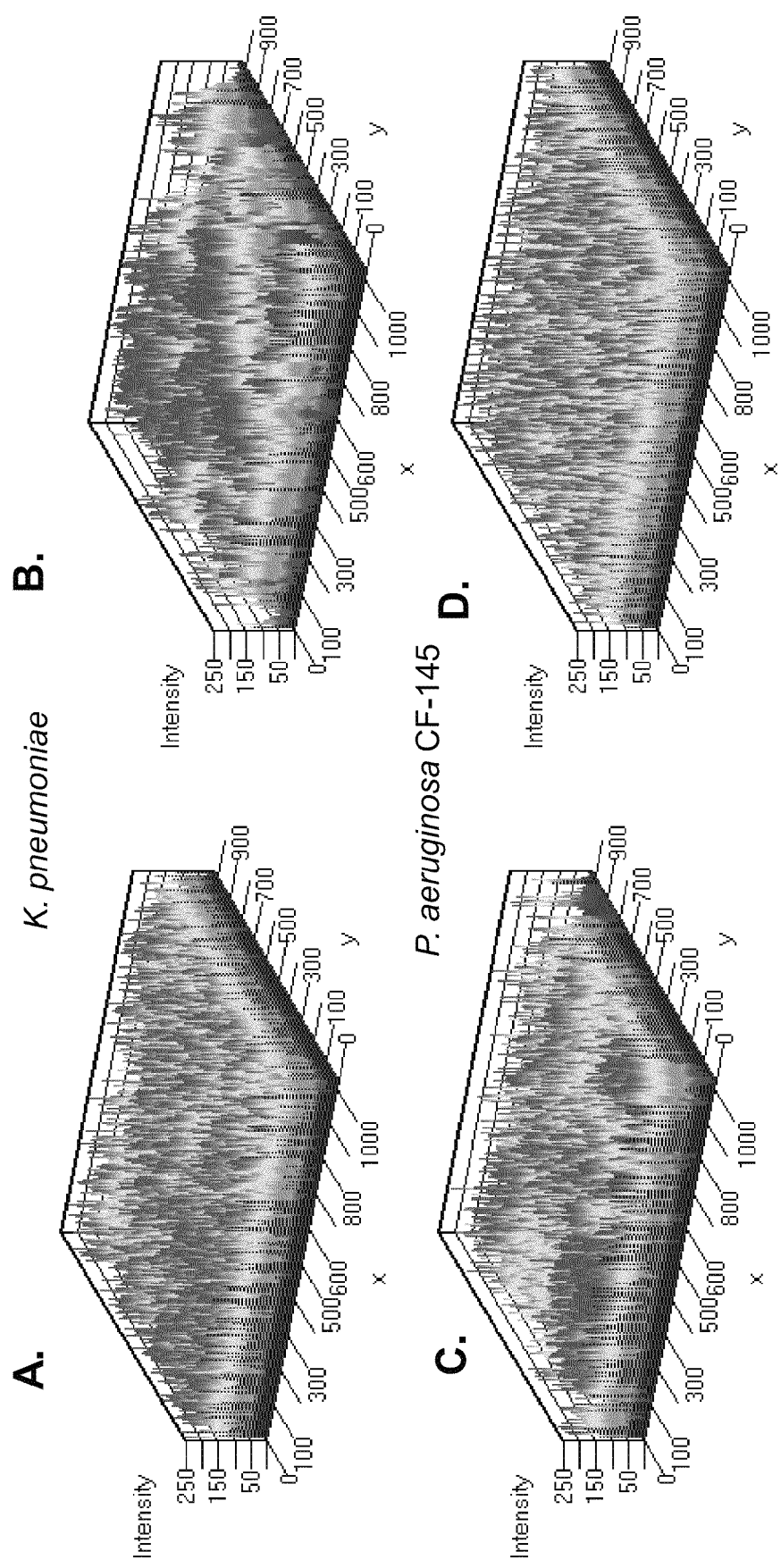
FIG. 7 shows that ABC-1 does not completely disperse pre-formed biofilms according to illustrative embodiments of the present invention. Three-dimensional view of biofilm formation in flow cells is shown through intensity mapping of *K. pneumonia* (A and B) and *P. aeruginosa* CF-145 (C and D).

In the experiments described thus far, ABC-1 was added concurrently with inoculation of the bacteria. The inventors then examined whether ABC-1 was capable of dispersing pre-formed biofilms. For these experiments, ABC-1 was introduced at 24 hours to developed biofilms of *K. pneumoniae* and *P. aeruginosa* under flow conditions. After an additional 3, 6, and 24-hour incubation, the treated and untreated biofilms were visualized by CLSM to determine if dispersal had occurred. Our results indicate that ABC-1 addition to preformed biofilms did not confer any significant changes in biofilm architecture, at least in the conditions examined here (FIG. 7 A-D).

Surface Coated ABC-1 Reduces Biofilm Formation

Biofilm-based bacterial disease is often associated with biofilm development on indwelling medical devices such as catheters and joint replacements (18). One strategy for reducing these infections is to treat the surfaces with antimicrobials or anti-biofilm compounds to prevent the formation of biofilms.

Figure 8:
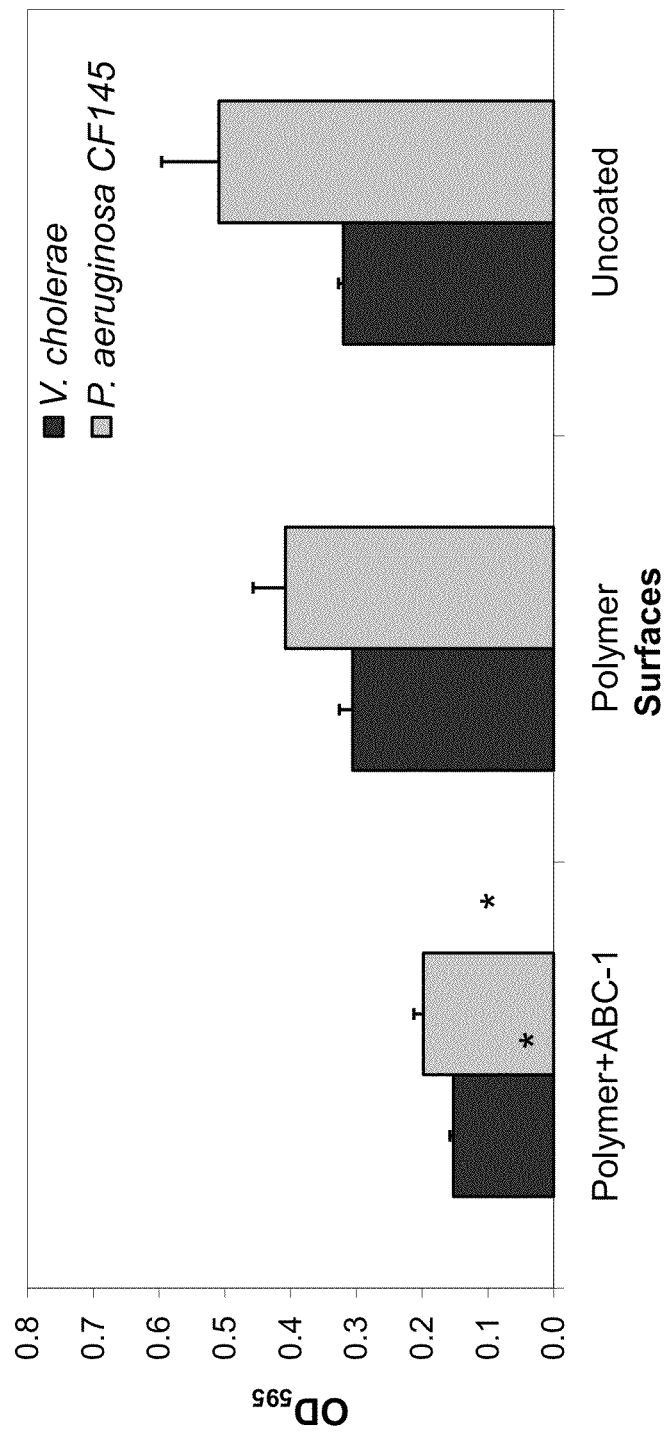
FIG. 8 shows that a coating of ABC-1 applied to a surface reduces biofilm formation, according to illustrative embodiments of the present invention. Cultures of *V. cholerae* and *P. aeruginosa* were allowed to form biofilms on the pegs of an MBEC plate that were coated with polymer and ABC-1, polymer only, or uncoated. Biofilm was quantified by staining the pegs with crystal violet and elution with ethanol as described in text. The results represent the mean±SEM from at least three independent experiments. A paired t test was used to compare the biofilm growth on uncoated surface to ABC-1 coated surface (*denotes statistical significance of $P<0.05$).
Figure 9:
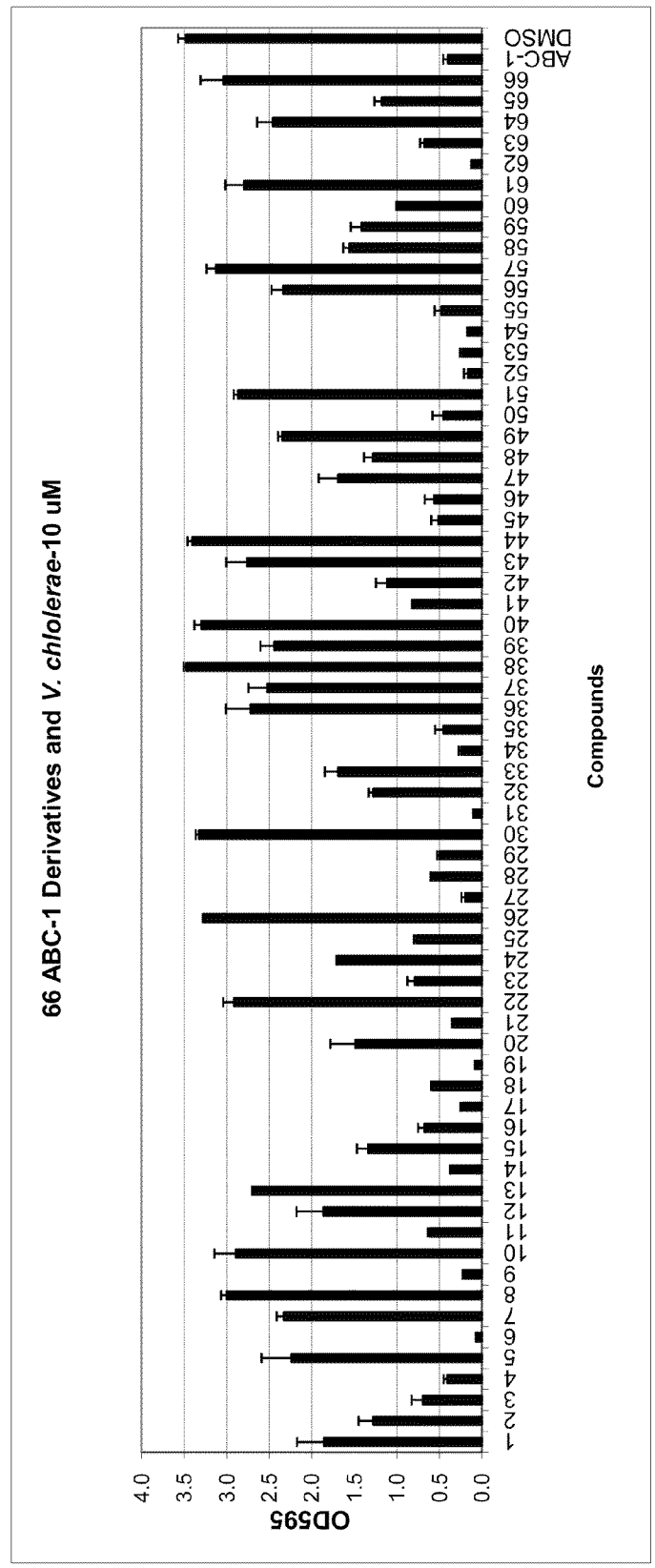
FIG. 9 shows the activity of the 66 ABC-1 derivatives according to illustrative embodiments of the present invention. The amount of biofilms formed by *V. cholerae* grown in the presence of 10 µM of each derivative was determined at 24 hours using the MBEC assay. Error bars represent the S.E.M. ABC-1 served as a positive control while DMSO was the negative control.
Figure 10:
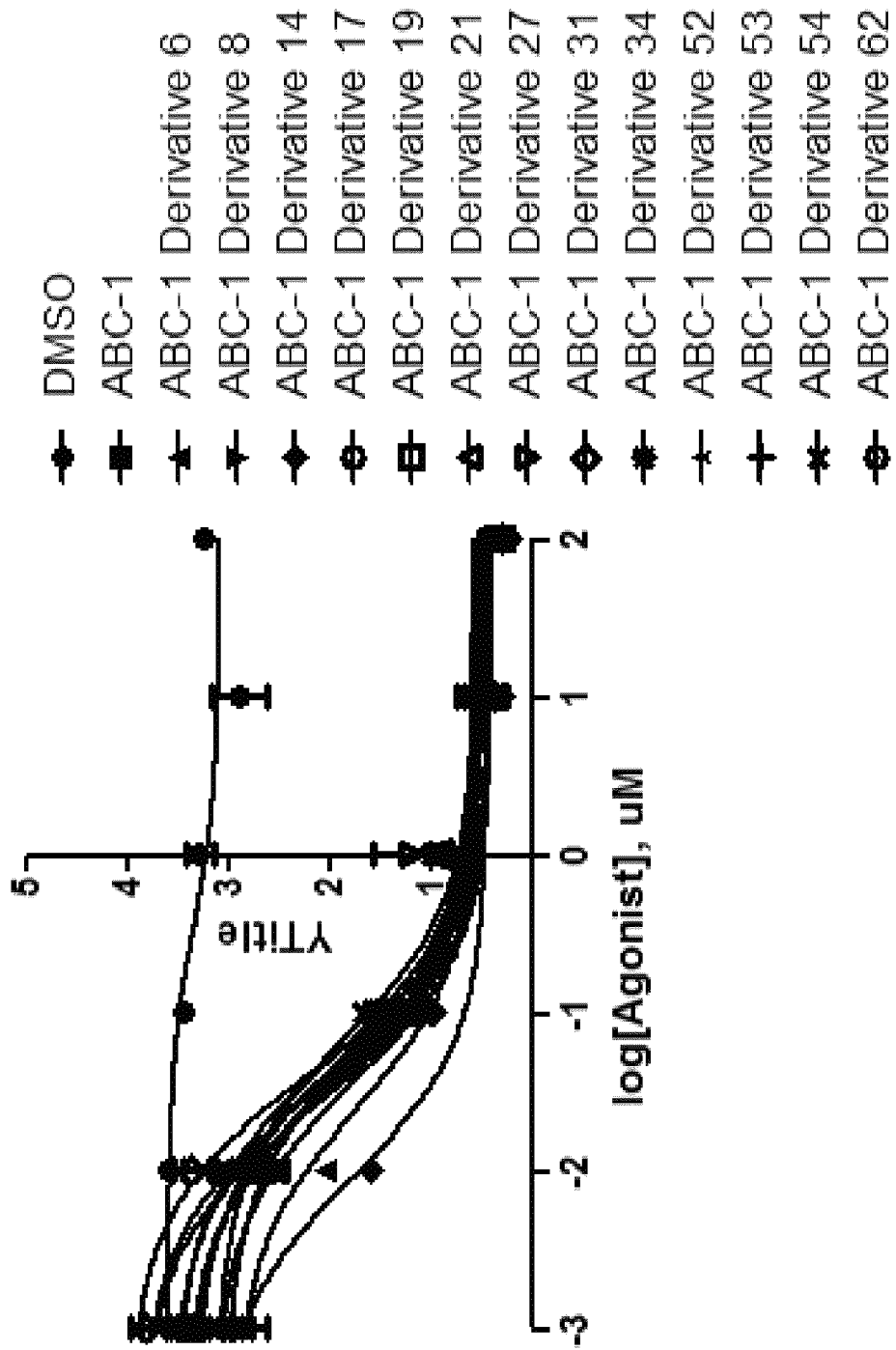
FIG. 10 shows dose response curves of ABC-1 and derivatives thereof against *V. cholerae* biofilms. The $IC_{50}$ concentration at which each of the most active ABC-1 derivatives inhibited biofilms in *V. cholerae* was determined in duplicate according to illustrative embodiments of the present invention. The data were fit to a log(inhibitor) vs. response curve using a nonlinear regression with variable slope analysis by the software Prism.
Figure 11:
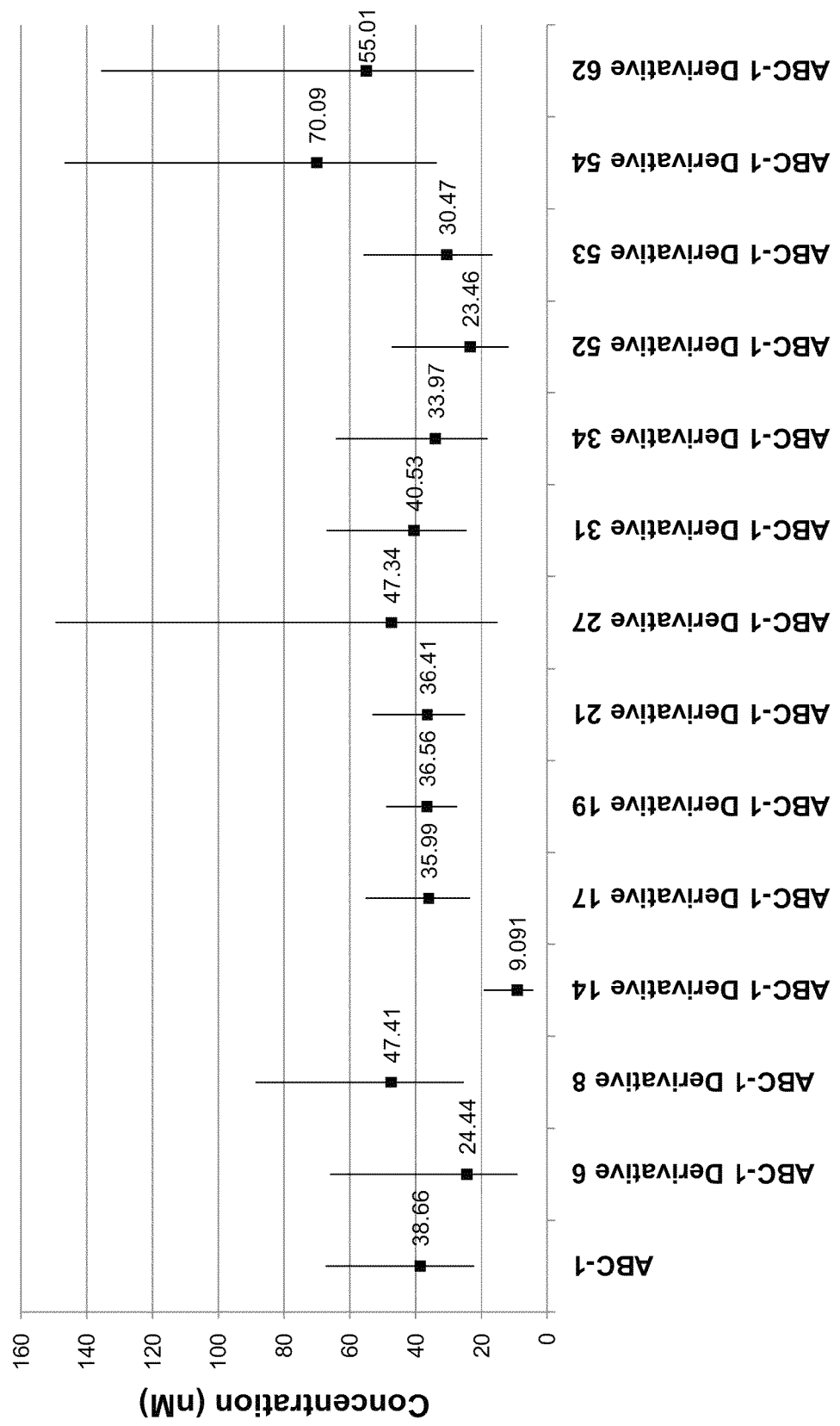
FIG. 11 shows IC50 values for ABC-1 and derivatives thereof. As shown, the ABC-derivative 14 is significantly more active according to illustrative embodiments of the present invention. The IC50 concentration where each derivative inhibited biofilms is shown with 95% confidence intervals as determined from the data shown in FIG. 10.

To determine if ABC-1 can be used in this manner, ABC-1 was coated onto the polystyrene surfaces of MBEC pegs using pH-sensitive polyelectrolyte multilayers (see discussion). Biofilm formation of *V. cholerae* and a *P. aeruginosa* CF-145 was then measured on regular MBEC pegs, MBEC pegs coated with the polymer only, and MBEC pegs coated with the polymer containing ABC-1. Our results showed that biofilm formation of both pathogens was reduced at least 50% when compared to the untreated or the polyelectrolyte control surfaces (FIG. 8), indicating that ABC-1 can be effectively targeted to relevant surfaces to prevent biofilms.

ABC-1 does not Impact c-di-GMP Signaling

The inventors hypothesized that ABC-1 could inhibit biofilms through inhibition of c-di-GMP signaling. To test this, the levels of c-di-GMP were examined in both *V. cholerae* and *P. aeruginosa* PA01 treated with and without 35 µM ABC-1. Growth of *V. cholerae* in ABC-1 led to a modest reduction in intracellular c-di-GMP, but ABC-1 had no effect on the levels of c-di-GMP in *P. aeruginosa* (data not shown). Furthermore, we established an in vitro assay to measure the activity of the diguanylate cyclase (DGC) enzyme VC2370 that synthesizes c-di-GMP and the phosphodiesterase (PDE) enzyme VieA that degrades c-di-GMP. ABC-1 had no significant impact on the in vitro activity of these enzymes at any concentration examined (data not shown). Finally, *S. aureus* is not predicted to encode the enzymes necessary to synthesize and degrade c-di-GMP, yet ABC-1 was able to inhibit biofilm formation in this species of bacteria. Therefore, we conclude that ABC-1 is inhibiting biofilm formation through an unknown mechanism that is independent of c-di-GMP signaling. The mechanism by which ABC-1 exerts anti-biofilm activity is currently under investigation.

EXAMPLE 2

Testing was carried out according to the following procedures:

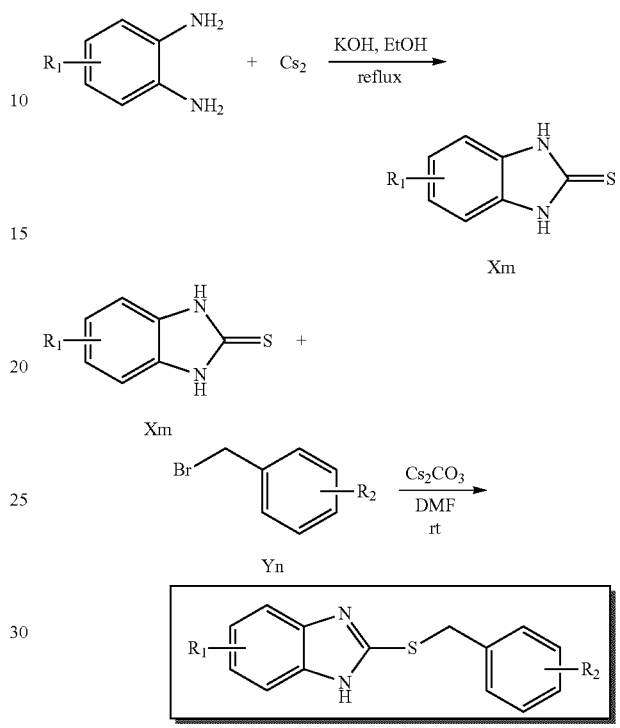

wherein for this schematic diagram of the synthetic process: $R_1$ and $R_2$ are substituents or ring structures present on the compounds described herein.

Thus, $R_1$ can generally be a linear or branched alkyl, halo, nitro, alkoxy, or $R_1$ forms a cyclic, heterocyclic or aromatic ring that includes an adjacent carbon atom in the benzene ring of the Xm or XmYn indoline-2-thiol; and $R_2$ is generally hydrogen, linear or branched alkyl, halo, alkoxy, or $R_2$ forms a cyclic, heterocyclic or aromatic ring that includes an adjacent carbon atom in the benzene ring; in some embodiments the aromatic ring joined to the $R_2$ group is a heteroaromatic ring (with 1-3 nitrogen, oxygen or sulfur heteroatoms).

To a solution of diamine (10 mmol) in the mixture of ethanol and water (v/v 12/2 mL) was added KOH (0.7 g, 12.5 mmol) followed by CS2 (0.7 mL, 11.6 mmol). The suspension was stirred for 10 min at rt then 3-4.5 h at reflux (oil bath 90-95° C.). After the solution cooled, charcoal (0.5 g) was added and then the mixture was refluxed for another 15 min. After filtration, the filtrate was heated to 60-70° C. and water (12 mL) was added followed by HOAc (0.85 mL) in water (1.7 mL) dropwise with good stirring. The solution was allowed to stand for 0.5 h at rt then 3 h in the refrigerator to complete the crystallization. The product was collected by filtration and washed with water (3×10 mL) and hexanes (3×10 mL), dried under vacuum to provide the desired Xm in 60-80% yield. (In general, the crude product was pure enough.) At 0° C., to the mixture of Xm (0.533 mmol) and Yn (0.533 mmol) in DMF (2 mL) was added $Cs_2CO_3$ (0.26 g, 0.8 mmol) and the suspension was stirred for 2-2.5 h at 0° C. Cold water (10 mL) was added to the reaction dropwise with vigorous stirring. After being stirred for 20 min at rt, the crude product was collected by filtration, rinsed with water (3×5 mL) and hexanes (3×5 mL), and dried under vacuum. Some of products gave a very pure sample at this stage. Some of them needed the purification using column chromatography (8:1-3:1 hexanes/EtOAc) or re-crystallization (EtOH/H2O or EtOAc/hexanes). The yield was in the range 70-98%.

CONCLUSION

In the various embodiments described herein, a novel benzimidazole anti-biofilm compound, ABC-1 is provided. The compound can inhibit biofilm formation in biofilm-forming pathogens and has a low toxicity.

Additionally, the presence of ABC-1 in medical devices is not expected to cause an inflammatory response. As such, medical devices comprising ABC-1 are also provided. In one embodiment, the potential anti-inflammatory activity of ABC-1 may be beneficial in treating chronic infections of various types. In one embodiment, ABC-1 is used to treat chronic infections in a cystic fibrosis lung, where it is thought that host inflammation is responsible for much of the host-cell damage observed.

In contrast to known compounds such as 2-aminobenzimidazoles, ABC-1 exhibits broad spectrum activity against multiple gram-negative bacteria including, for example, *P. aeruginosa*. This may be due to increased diffusion of ABC-1 across the outer membrane of gram-negative bacteria compared with the 2-aminobenzimidazoles.

The increased prevalence of antibiotic resistant bacteria heralds a need for new drugs and novel strategies to identify better drug targets. Co-administration of antibiotics and anti-biofilm molecules could form the basis of future clinical protocols against biofilm-based infections.

Additionally, biofilm encroachment of biomaterial is a concern post-surgery. In one embodiment, the anti-bacterial compound ABC-1 is incorporated in a multilayer biomaterial assembly at low pH. The compound can be released due to disruption in H-bonding when the films were immersed in solutions with neutral pH. In one embodiment, surfaces modified with ABC-1 are able to significantly inhibit biofilm formation of *V. cholerae* and a cystic fibrosis isolate of *P. aeruginosa*.

Although specific embodiments have been illustrated and described herein, it will be appreciated by those of ordinary skill in the art that any procedure that is calculated to achieve the same purpose may be substituted for the specific embodiments shown. This application is intended to cover any adaptations or variations of the present subject matter. Therefore, it is manifestly intended that embodiments of this invention be limited only by the claims and the equivalents thereof.

What is claimed is:

1. A compound comprising:

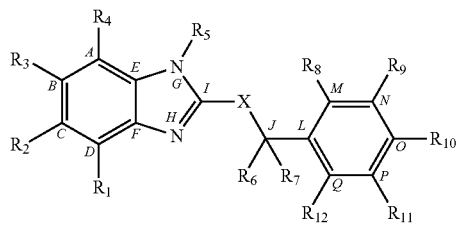

wherein $R_1$, $R_2$, $R_3$, $R_4$, $R_5$, $R_6$, $R_7$, $R_8$, $R_9$, $R_{10}$, $R_{11}$, and $R_{12}$ are each independently hydrogen, alkyl, alkenyl, alkynyl, aryl, heteroaryl, heterocyclyl, alkoxy, aryloxy, heteroaryloxy, alkoxycarbonyl, aryloxycarbonyl, heteroaryloxycarbonyl, alkylsulfonyl, arylsulfonyl, aminosulfonyl, alkylcarbonyl, arylcarbonyl, heteroarylcarbonyl, acyl, acylamino, amino, alkylamino, dialkylamino, acylamino, carboxylate (—$CO_2H$), cyano, nitro, —$CONH_2$, heteroarylamino, oxime, alkyloxime, aryloxime, amino-oxime or halogen when A, B, C, D, E, F, G, H, I, J, K, L, M, N, O, P, and Q are carbon, and X is O, NR (where R is hydrogen, alkyl, aryl or acyl), S, SO (sulfoxide), $SO_2$ (sulfone), or $C(R)_2$ (where R=H, alkyl, aryl, alkenyl, alkynyl, or acyl); or wherein $R_1$, $R_2$, $R_3$, $R_4$, $R_5$, $R_6$, $R_7$, $R_8$, $R_9$, $R_{10}$, $R_{11}$, and $R_{12}$ are each independently hydrogen or hydroxyl when A, B, C, D, E, F, G, H, I, J, K, L, M, N, O, P, and Q are each independently nitrogen, and combinations, pharmaceutically acceptable salts, esters, and prodrugs thereof.

2. A composition comprising a compound of claim 1 and a carrier.

3. A medical device comprising one or more compounds of the following formula:

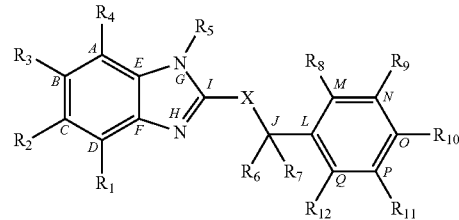

wherein $R_1$, $R_2$, $R_3$, $R_4$, $R_5$, $R_6$, $R_7$, $R_8$, $R_9$, $R_{10}$, $R_{11}$, and $R_{12}$ are each independently hydrogen, alkyl, alkenyl, alkynyl, aryl, heteroaryl, heterocyclyl, alkoxy, aryloxy, heteroaryloxy, alkoxycarbonyl, aryloxycarbonyl, heteroaryloxycarbonyl, alkylsulfonyl, arylsulfonyl, aminosulfonyl, alkylcarbonyl, arylcarbonyl, heteroarylcarbonyl, acyl, acylamino, amino, alkylamino, dialkylamino, arylamino, carboxylate (—$CO_2H$), cyano, nitro, $CONH_2$, heteroarylamino, oxime, alkyloxime, aryloxime, amino-oxime or halogen when A, B, C, D, E, F, G, H, I, J, K, L, M, N, O, P, and Q are carbon, and X is O, NR (where R is hydrogen, alkyl, aryl or acyl), S, SO (sulfoxide), $SO_2$ (sulfone), or $C(R)_2$ (where R=H, alkyl, aryl, alkenyl, alkynyl, or acyl); or wherein $R_1$, $R_2$, $R_3$, $R_4$, $R_5$, $R_6$, $R_7$, $R_8$, $R_9$, $R_{10}$, $R_{11}$, and $R_{12}$ are each independently hydrogen or hydroxyl when A, B, C, D, E, F; G, H, I, J, K, L, M, N, O, P, and Q are each independently nitrogen, and combinations, pharmaceutically acceptable salts, esters, and prodrugs thereof.

4. A method of treating an infection by a pathogen comprising administering to a mammal infected with the pathogen a compound of the following formula:

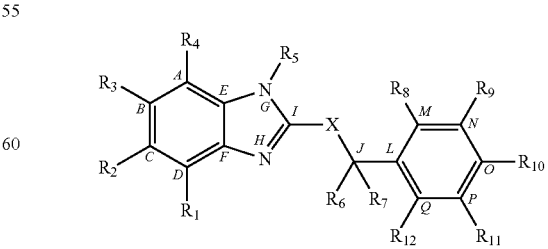

wherein $R_1$, $R_2$, $R_3$, $R_4$, $R_5$, $R_6$, $R_7$, $R_8$, $R_9$, $R_{10}$, $R_{11}$, and $R_{12}$ are each independently hydrogen, alkyl, alkenyl, alkynyl, aryl, heteroaryl, heterocyclyl, alkoxy, aryloxy, heteroaryloxy, alkoxycarbonyl, aryloxycarbonyl, heteroaryloxycarbonyl, alkylsulfonyl, arylsulfonyl, aminosulfonyl, alkylcarbonyl, arylcarbonyl, heteroarylcarbonyl, acyl, acylamino, amino, alkylamino, dialkylamino, arylamino, carboxylate ($-CO_2H$), cyano, nitro, $CONH_2$, heteroarylamino, oxime, alkyloxime, aryloxime, amino-oxime or halogen when A, B, C, D, E, F, G, H, I, J, K, L, M, N, O, P, and Q are carbon, and X is O, NR (where R is hydrogen, alkyl, aryl or acyl), S, SO (sulfoxide), $SO_2$ (sulfone), or $C(R)_2$ (where R=H, alkyl, aryl, alkenyl, alkynyl, or acyl); or wherein $R_1$, $R_2$, $R_3$, $R_4$, $R_5$, $R_6$, $R_7$, $R_8$, $R_9$, $R_{10}$, $R_{11}$, and $R_{12}$ are each independently hydrogen or hydroxyl when A, B, C, D, E, F, G, H, I, J, K, L, M, N, O, P, and Q are each independently nitrogen, and combinations, pharmaceutically acceptable salts, esters, and prodrugs thereof.

5. The method of claim 4, wherein the compound or a combination thereof is administered topically or locally.

6. The method of claim 4, wherein the compound or a combination thereof is administered to the site of an infection.

7. The method of claim 4, wherein the pathogen is a gram negative bacterium.

8. The method of claim 4, wherein the pathogen is a gram positive bacteria.

9. The method of claim 4, wherein the pathogen is a drug-resistant pathogen.

10. The method of claim 4, wherein the pathogen is selected from *Vibrio cholerae, P. aeruginosa, Klebsiella pneumoniae, Erwinia amylovora, Shigella boydii, Staphylococcus aureus* and combinations thereof.

11. The method of claim 4, wherein the infection by a pathogen is related, or leads, to endocarditis, otitis media, chronic prostatitis, periodontal disease, chronic urinary tract infection, cystic fibrosis, an infection on an indwelling medical device, or a chronic non-healing wound.

12. The method of claim 4, wherein a therapeutically effective amount is administered.

13. The method of claim 12, wherein a therapeutically effective amount is an amount effective to inhibit biofilm formation by the pathogen.

14. A method of inhibiting biofilm formation in biofilm-forming pathogens comprising contacting the pathogen with the compound of claim 1 to thereby inhibit biofilm formation of the pathogen.

15. The method of claim 14, wherein contacting comprises administering or applying the compound to a surface suspected of containing the pathogen.

* * * * *

UNITED STATES PATENT AND TRADEMARK OFFICE
CERTIFICATE OF CORRECTION

PATENT NO. : 8,710,082 B2  
APPLICATION NO. : 13/366278  
DATED : April 29, 2014  
INVENTOR(S) : Christopher Waters et al.

It is certified that error appears in the above-identified patent and that said Letters Patent is hereby corrected as shown below:

ON THE TITLE PAGE:

Item (73) Assignee: Please add "University of Medicine & Dentistry of New Jersey, Somerset, NJ (US); The Trustees of Princeton University, Princeton, NJ (US)"

Signed and Sealed this
Seventeenth Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO.         : 8,710,082 B2
APPLICATION NO.    : 13/366278
DATED              : April 29, 2014
INVENTOR(S)        : Christopher Waters et al.

It is certified that error appears in the above-identified patent and that said Letters Patent is hereby corrected as shown below:

On the Title Page, Item (57)

Abstract/ Line 10: Error reads as "–CONH2," and should read as "–CONH$_2$"

In the Specification

Pat. Col 3/Line 46: Error reads as "log(inhibitor)" and should read as "log (inhibitor)"
Pat. Col 3/Line 49: Error reads as "IC50" and should read as "IC$_{50}$"
Pat. Col 3/Line 52: Error reads as "IC50" and should read as "IC$_{50}$"

Pat. Col 4/Line 65 to Pat. Col 6/Line 12: Error reads as:
"2-(benzylthio)-1H-benzo[d]imidazole
2-(4-methylbenzylthio)-1H-benzo[d]imidazole
2-(4-methoxybenzylthio)-1H-benzo[d]imidazole
2-(4-isopropylbenzylthio)-1H-benzo[d]imidazole
2-(3-methylbenzylthio)-1H-benzo[d]imidazole
2-(2-fluorobenzylthio)-1H-benzo[d]imidazole
2-(3-fluorobenzylthio)-1H-benzo[d]imidazole
2-(naphthalen-2-ylmethylthio)-1H-benzo[d]imidazole
2-(pyridin-4-ylmethylthio)-1H-benzo[d]imidazole
2-(benzylthio)-5-methyl-1H-benzo[d]imidazole
5-methyl-2-(4-methylbenzylthio)-1H-benzo[d]imidazole
2-(4-methoxybenzylthio)-5-methyl-1H-benzo[d]imidazole
2-(4-isopropylbenzylthio)-5-methyl-1H-benzo[d]imidazole
5-methyl-2-(3-methylbenzylthio)-1H-benzo[d]imidazole
2-(2-fluorobenzylthio)-5-methyl-1H-benzo[d]imidazole
2-(3-fluorobenzylthio)-5-methyl-1H-benzo[d]imidazole
5-methyl-2-(naphthalen-2-ylmethylthio)-1H-benzo[d]imidazole Signed and Sealed this
Twenty-sixth Day of August, 2014

Michelle K. Lee
*Deputy Director of the United States Patent and Trademark Office*

CERTIFICATE OF CORRECTION (continued)
U.S. Pat. No. 8,710,082 B2

Pat. Col 4/Line 65 to Pat. Col 6/Line 12: Error reads as (CONTINUED FROM PAGE 1):

2-(benzylthio)-5-methoxy-1H-benzo[d]imidazole
5-methoxy-2-(pyridin-4-ylmethylthio)-1H-benzo[d]imidazole
5-methoxy-2-(3-methoxybenzylthio)-1H-benzo[d]imidazole
5-methoxy-2-(4-methoxybenzylthio)-1H-benzo[d]imidazole
2-(4-isopropylbenzylthio)-5-methoxy-1H-benzo[d]imidazole
5-methoxy-2-(3-methylbenzylthio)-1H-benzo[d]imidazole
2-(2-fluorobenzylthio)-5-methoxy-1H-benzo[d]imidazole
2-(3-fluorobenzylthio)-5-methoxy-1H-benzo[d]imidazole
5-methoxy-2-(naphthalen-2-ylmethylthio)-1H-benzo[d]imidazole
2-(benzylthio)-5-fluoro-1H-benzo[d]imidazole
5-fluoro-2-(4-methylbenzylthio)-1H-benzo[d]imidazole
5-fluoro-2-(4-methoxybenzylthio)-1H-benzo[d]imidazole
5-fluoro-2-(4-isopropylbenzylthio)-1H-benzo[d]imidazole
5-fluoro-2-(3-methylbenzylthio)-1H-benzo[d]imidazole
5-fluoro-2-(2-fluorobenzylthio)-1H-benzo[d]imidazole
5-fluoro-2-(3-fluorobenzylthio)-1H-benzo[d]imidazole
5-fluoro-2-(naphthalen-2-ylmethylthio)-1H-benzo[d]imidazole
2-(benzylthio)-5-chloro-1H-benzo[d]imidazole
5-chloro-2-(4-methylbenzylthio)-1H-benzo[d]imidazole
5-chloro-2-(4-methoxybenzylthio)-1H-benzo[d]imidazole
5-chloro-2-(4-isopropylbenzylthio)-1H-benzo[d]imidazole
5-chloro-2-(3-methylbenzylthio)-1H-benzo[d]imidazole
5-chloro-2-(2-fluorobenzylthio)-1H-benzo[d]imidazole
5-chloro-2-(3-fluorobenzylthio)-1H-benzo[d]imidazole
5-chloro-2-(naphthalen-2-ylmethylthio-1H-benzo[d]imidazole
2-(benzylthio)-5-nitro-1H-benzo[d]imidazole
2-(4-methylbenzylthio)-5-nitro-1H-benzo[d]imidazole
2-(4-methoxybenzylthio)-5-nitro-1H-benzo[d]imidazole
2-(4-isopropylbenzylthio)-5-nitro-1H-benzo[d]imidazole
2-(3-methylbenzylthio-5-nitro-1H-benzo[d]imidazole
2-(2-fluorobenzylthio)-5-nitro-1H-benzo[d]imidazole
2-(3-fluorobenzylthio)-5-nitro-1H-benzo[d]imidazole
2-(napthalen-2-ylmethylthio)-5-nitro-1H-benzo[d]imidazole
2-(benzylthio)-1H-naphtho-[2,3-d]imidazole
2-(4-methylbenzylthio)-1H-naphtho[2,3-d]imidazole
2-(4-methoxybenzylthio)-1H-naphtho[2,3-d]imidazole
2-(4-isopropylbenzylthio)-1H-naphtho[2,3-d]imidazole
2-(3-methylbenzylthio)-1H-naphtho[2,3-d]imidazole
2-(2-fluorobenzylthio)-1H-naphtho[2,3-d]imidazole
2-(3-fluorobenzylthio)-1H-naphtho[2,3-d]imidazole
2-(naphthalen-2-ylmethylthio)-1H-naphtho[2,3-d]imidazole
2-(benzylthio)-5,6-dimethyl-1H-benzo[d]imidazole
5,6-dimethyl-2-(4-methylbenzylthio)-1H-benzo[d]imidazole
2-(4-methoxybenzylthio)-5,6-dimethyl-1H-benzo[d]imidazole

CERTIFICATE OF CORRECTION (continued)

Page 3 of 4

U.S. Pat. No. 8,710,082 B2

Pat. Col 4/Line 65 to Pat. Col 6/Line 12: Error reads as (CONTINUED FROM PAGE 2):
2-(4-isopropylbenzylthio)-5,6-dimethyl-1H-benzo[d]imidazole
5,6-dimethyl-2-(3-methylbenzylthio)-1H-benzo[d]imidazole
2-(2-fluorobenzylthio)-5,6-dimethyl-1H-benzo[d]imidazole
2-(3-fluorobenzylthio)-5,6-dimethyl-1H-benzo[d]imidazole
5,6-dimethyl-2-(naphthalen-2-ylmethylthio)-1H-benzo[d]imidazole"

Pat. Col 4/Line 65 to Pat. Col 6/Line 12 should read as:
"13.  2-(benzylthio)-1*H*-benzo[*d*]imidazole
21.  2-(4-methylbenzylthio)-1*H*-benzo[*d*]imidazole
14.  2-(4-methoxybenzylthio)-1*H*-benzo[*d*]imidazole
22.  2-(4-isopropylbenzylthio)-1*H*-benzo[*d*]imidazole
23.  2-(3-methylbenzylthio)-1*H*-benzo[*d*]imidazole
24.  2-(2-fluorobenzylthio)-1*H*-benzo[*d*]imidazole
25.  2-(3-fluorobenzylthio)-1*H*-benzo[*d*]imidazole
26.  2-(naphthalen-2-ylmethylthio)-1*H*-benzo[*d*]imidazole
64.  2-(pyridin-4-ylmethylthio)-1*H*-benzo[*d*]imidazole
27.  2-(benzylthio)-5-methyl-1*H*-benzo[*d*]imidazole
28.  5-methyl-2-(4-methylbenzylthio)-1*H*-benzo[*d*]imidazole
29.  2-(4-methoxybenzylthio)-5-methyl-1*H*-benzo[*d*]imidazole
30.  2-(4-isopropylbenzylthio)-5-methyl-1*H*-benzo[*d*]imidazole
33.  5-methyl-2-(3-methylbenzylthio)-1*H*-benzo[*d*]imidazole
34.  2-(2-fluorobenzylthio)-5-methyl-1*H*-benzo[*d*]imidazole
35.  2-(3-fluorobenzylthio)-5-methyl-1*H*-benzo[*d*]imidazole
36.  5-methyl-2-(naphthalen-2-ylmethylthio)-1*H*-benzo[*d*]imidazole
17.  2-(benzylthio)-5-methoxy-1*H*-benzo[*d*]imidazole
66.  5-methoxy-2-(pyridin-4-ylmethylthio)-1*H*-benzo[*d*]imidazole
15.  5-methoxy-2-(3-methoxybenzylthio)-1*H*-benzo[*d*]imidazole
18.  5-methoxy-2-(4-methoxybenzylthio)-1*H*-benzo[*d*]imidazole
5.   2-(4-isopropylbenzylthio)-5-methoxy-1*H*-benzo[*d*]imidazole
3.   5-methoxy-2-(3-methylbenzylthio)-1*H*-benzo[*d*]imidazole
9.   2-(2-fluorobenzylthio)-5-methoxy-1*H*-benzo[*d*]imidazole
4.   2-(3-fluorobenzylthio)-5-methoxy-1*H*-benzo[*d*]imidazole
12.  5-methoxy-2-(naphthalen-2-ylmethylthio)-1*H*-benzo[*d*]imidazole
37.  2-(benzylthio)-5-fluoro-1*H*-benzo[*d*]imidazole
38.  5-fluoro-2-(4-methylbenzylthio)-1*H*-benzo[*d*]imidazole
39.  5-fluoro-2-(4-methoxybenzylthio)-1*H*-benzo[*d*]imidazole
40.  5-fluoro-2-(4-isopropylbenzylthio)-1*H*-benzo[*d*]imidazole
41.  5-fluoro-2-(3-methylbenzylthio)-1*H*-benzo[*d*]imidazole
43.  5-fluoro-2-(2-fluorobenzylthio)-1*H*-benzo[*d*]imidazole
46.  5-fluoro-2-(3-fluorobenzylthio)-1*H*-benzo[*d*]imidazole
47.  5-fluoro-2-(naphthalen-2-ylmethylthio)-1*H*-benzo[*d*]imidazole
19.  2-(benzylthio)-5-chloro-1*H*-benzo[*d*]imidazole
20.  5-chloro-2-(4-methylbenzylthio)-1*H*-benzo[*d*]imidazole
16.  5-chloro-2-(4-methoxybenzylthio)-1*H*-benzo[*d*]imidazole

CERTIFICATE OF CORRECTION (continued)
U.S. Pat. No. 8,710,082 B2

Pat. Col 4/Line 65 to Pat. Col 6/Line 12 should read as (CONTINUED FROM PAGE 3):

1. 5-chloro-2-(4-isopropylbenzylthio)-1*H*-benzo[*d*]imidazole
2. 5-chloro-2-(3-methylbenzylthio)-1*H*-benzo[*d*]imidazole
6. 5-chloro-2-(2-fluorobenzylthio)-1*H*-benzo[*d*]imidazole
31. 5-chloro-2-(3-fluorobenzylthio)-1*H*-benzo[*d*]imidazole
32. 5-chloro-2-(naphthalen-2-ylmethylthio-1*H*-benzo[*d*]imidazole
62. 2-(benzylthio)-5-nitro-1*H*-benzo[*d*]imidazole
52. 2-(4-methylbenzylthio)-5-nitro-1*H*-benzo[*d*]imidazole
45. 2-(4-methoxybenzylthio)-5-nitro-1*H*-benzo[*d*]imidazole
49. 2-(4-isopropylbenzylthio)-5-nitro-1*H*-benzo[*d*]imidazole
53. 2-(3-methylbenzylthio-5-nitro-1*H*-benzo[*d*]imidazole
50. 2-(2-fluorobenzylthio)-5-nitro-1*H*-benzo[*d*]imidazole
54. 2-(3-fluorobenzylthio)-5-nitro-1*H*-benzo[*d*]imidazole
56. 2-(naphthalen-2-ylmethylthio)-5-nitro-1*H*-benzo[*d*]imidazole
10. 2-(benzylthio)-1*H*-naphtho-[2,3-*d*]imidazole
8. 2-(4-methylbenzylthio)-1*H*-naphtho[2,3-*d*]imidazole
51. 2-(4-methoxybenzylthio)-1*H*-naphtho[2,3-*d*]imidazole
57. 2-(4-isopropylbenzylthio)-1*H*-naphtho[2,3-*d*]imidazole
58. 2-(3-methylbenzylthio)-1*H*-naphtho[2,3-*d*]imidazole
11. 2-(2-fluorobenzylthio)-1*H*-naphtho[2,3-*d*]imidazole
7. 2-(3-fluorobenzylthio)-1*H*-naphtho[2,3-*d*]imidazole
61. 2-(naphthalen-2-ylmethylthio)-1*H*-naphtho[2,3-*d*]imidazole
55. 2-(benzylthio)-5,6-dimethyl-1*H*-benzo[*d*]imidazole
42. 5,6-dimethyl-2-(4-methylbenzylthio)-1*H*-benzo[*d*]imidazole
48. 2-(4-methoxybenzylthio)-5,6-dimethyl-1*H*-benzo[*d*]imidazole
44. 2-(4-isopropylbenzylthio)-5,6-dimethyl-1*H*-benzo[*d*]imidazole
60. 5,6-dimethyl-2-(3-methylbenzylthio)-1*H*-benzo[*d*]imidazole
63. 2-(2-fluorobenzylthio)-5,6-dimethyl-1*H*-benzo[*d*]imidazole
65. 2-(3-fluorobenzylthio)-5,6-dimethyl-1*H*-benzo[*d*]imidazole
59. 5,6-dimethyl-2-(naphthalen-2-ylmethylthio )-1*H*-benzo[*d*]imidazole"

Pat. Col 18/Line 63: Error reads as "$M_y$" and should read as "$M_w$"
Pat. Col 19/Line 9: Error reads as "Broading" and should read as "Boarding"
Pat. Col 20/Line 47: Error reads as "log(inhibitor)" and should read as "log (inhibitor)"
Pat. Col. 25/Line 5: Error reads as "re-crystallization" and should read as "re-crystallization."
Pat. Col 26/Line 5: Error reads as "acylamino" and should read as "arylamino"
Pat. Col 26/Line 47: Error reads as "F;" and should read as "F,"